US006699879B1

(12) United States Patent
Coulton et al.

(10) Patent No.: US 6,699,879 B1
(45) Date of Patent: Mar. 2, 2004

(54) PHENYL UREA AND PHENYL THIOUREA DERIVATIVES AS OREXIN RECEPTOR ANTAGONISTS

(75) Inventors: Steven Coulton, Horsham (GB); Amanda Johns, St Albans (GB); Roderick Alan Porter, Ashwell (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/913,236

(22) PCT Filed: Feb. 10, 2000

(86) PCT No.: PCT/EP00/01150

§ 371 (c)(1),
(2), (4) Date: Apr. 29, 2002

(87) PCT Pub. No.: WO00/47577

PCT Pub. Date: Aug. 17, 2000

(30) Foreign Application Priority Data

Feb. 12, 1999 (GB) .............................................. 9903266
Nov. 8, 1999 (GB) .............................................. 9926430

(51) Int. Cl.[7] ...................... A61K 31/47; C07D 215/38; C07D 215/18

(52) U.S. Cl. ...................... 514/313; 546/160; 546/162; 546/180

(58) Field of Search .......................... 514/313; 546/160, 546/162, 180

(56) References Cited

U.S. PATENT DOCUMENTS 5,552,411 A 9/1996 Downing et al.

FOREIGN PATENT DOCUMENTS

| | | | | |
|---|---|---|---|---|
| WO | WO 9418170 | * | 8/1994 | |
| WO | WO 98/08846 | | 3/1998 | C07D/471/04 |
| WO | WO 98/58905 | | 12/1998 | C07C/257/22 |
| WO | WO 99/09024 | | 2/1999 | C07D/401/12 |
| WO | WO 99/17775 | | 4/1999 | A61K/31/47 |
| WO | WO 99/38846 | | 8/1999 | C07D/215/50 |
| ZA | 9600497 | * | 8/1996 | |

OTHER PUBLICATIONS

Amaresh, Ramiya, abastract CA 130:66376, abstract of Tetrahedron, 1998, 54(47), 14327–14340.*

R. Amaresh and P. Perumal, "A Novel One–Pot Synthesis of 2–Aminoquinolines . . . Under Vilsmeier Conditions", Tetrahedron, vol. 54, No. 47, pp. 14327–14340 (1998).

* cited by examiner

*Primary Examiner*—D. Margaret Seaman
(74) *Attorney, Agent, or Firm*—Kathryn L. Sieburth; Mary E. McCarthy; Charles E. Kinzig

(57) ABSTRACT

The present invention provides phenyl urea and phenyl thiourea derivatives which are non-peptide antagonists of human orexin receptors, in particular orexin-1 receptors, of formula (I)

(I)

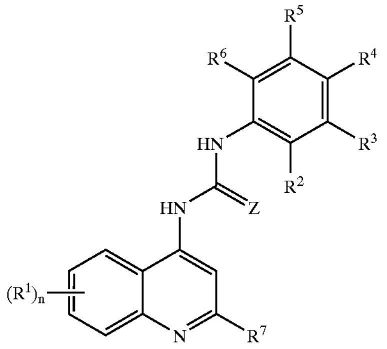

in which:

Z represents oxygen or sulfur; and $R^1$ to $R^7$ represent various substituent groups; and pharmaceutically acceptable salts thereof. In particular, these compounds are of potential use in the treatment of obesity including obesity observed in Type 2(non-insulin-dependent) diabetes patients and/or sleep disorders.

20 Claims, No Drawings

PHENYL UREA AND PHENYL THIOUREA DERIVATIVES AS OREXIN RECEPTOR ANTAGONISTS

This application is a 371 of PCT/EP00/01150, filed Feb. 10, 2000.

This invention relates to phenyl urea and phenyl thiourea derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlicli's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kaliman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell,* 1998, 92, 573–585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westemised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides phenyl urea and phenyl thiourea derivatives which are non-peptide antagonists of human orexin receptors, in particular orexin-1 receptors. In particular, these compounds are of potential use in the treatment of obesity including obesity observed in Type 2 (non-insulin-dependent) diabetes patients and/or sleep disorders.

Several phenyl urea derivatives are known in the literature, viz:

WO 93/18028, WO 94/14801 and WO 94/18170 disclose indolylurea, benzo[b]thienylurea and N-phenyl-N'-heteroarylurea derivatives respectively [compounds a)-i) below] as $5HT_2C$ receptor antagonists;

JP 04178362 discloses the compound N-(2-methyl-4-quinolinyl)-N'-(5,6,7,8-tetrahydro-1-naphthalenyl)urea [compound j) below] as an agrochemical pesticide;

EP 123146 discloses the compound N-(2-methyl-4-quinolinyl)-N'-(3,4,5-trimethoxyphenyl)urea [compound k) below] as an anti-inflammatory agent;

GB 2009155 and *J. Am. Chem. Soc.,* 1956, 78, 3703, disclose various N-phenyl-N'-(2-methyl-4-quinolinyl) urea derivatives [compounds m)-r) and compounds s)-w) below respectively];

*J. Serb. Chem. Soc.,* 1993, 58(10), 73743, discloses the synthesis of the compound N-(1,2-dihydro-6-methyl-2-oxo-4-quinolinyl)-N'-phenylthiourea [compound x) below];

none of these documents suggest the use of phenyl urea derivatives as orexin receptor antagonists.

International Patent Applications PCT/GB98/02437 and PCT/EP99/0300 (published after the priority date of the present application) disclose various phenyl urea derivatives as orexin receptor antagonists.

The present invention relates to N-phenyl-N'-(2-substituted-quinolinyl)urea derivatives which are non-peptide antagonists of human orexin receptors, in particular orexin-1 receptors. In particular, these compounds are of potential use in the treatment of obesity including obesity observed in Type 2 (non-insulin-dependent) diabetes patients and/or sleep disorders.

Thus according to the invention there is provided a compound of formula (I):

(I)

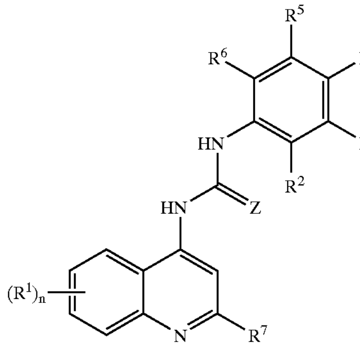

in which:

Z represents oxygen or sulfur;

$R^1$ represents $(C_{1-6})$alkyl, $(C_{2-6})$alkenyl or $(C_{1-6})$alkoxy, any of which may be optionally substituted; halogen, $R^8CO$— or $NR^9R^{10}CO$—;

$R^2$, $R^3$, $R^4$, $R^5$ and $R^6$ independently represent $(C_{1-6})$ alkyl, $(C_{2-6})$alkenyl, $(C_{1-6})$alkoxy or $(C_{1-6})$alkylthio, any of which may be optionally substituted; hydrogen, halogen, nitro, cyano, aryloxy, aryl$(C_{1-6})$alkyloxy, aryl $(C_{1-6})$alkyl, $R^8CO$—, $R^8SO_2NH$—, $R^8SO_2O$—, $R^8CON(R^{11})$—, $NR^9R^{10}$—, $NR^9R^{10}CO$—, —$COOR^9$, $R^{11}C({=}NOR^8)$, heterocyclyl or heterocyclyl$(C_{1-6})$ alkyl;

or an adjacent pair of $R^2$, $R^3$, $R^4$, $R^5$ and $R^6$ together with the carbon atoms to which they are attached form an optionally substituted carbocyclic or heterocyclic ring;

$R^7$ is $(C_{1-6})$alkyl, $(C_{2-6})$alkenyl, $(C_{1-6})$alkoxy or $(C_{1-6})$ alkylthio, any of which may be optionally substituted; halogen, hydroxy, nitro, cyano, $NR^9R^{10}$—, $NR^9R^{10}CO$—, $N_3$, —$OCOR^9$ or $R^8CON(R^{11})$—;

$R^8$ is $(C_{1-6})$alkyl, $(C_{2-6})$alkenyl, heterocyclyl, heterocyclyl$(C_{1-6})$alkyl, heterocyclyl$(C_{2-6})$alkenyl, aryl, aryl$(C_{1-6})$alkyl or aryl$(C_{2-6})$alkenyl, any of which maybe optionally substituted;

$R^9$ and $R^{10}$ independently represent hydrogen, $(C_{1-6})$ alkyl, $(C_{2-6})$alkenyl, heterocyclyl, heterocyclyl$(C_{1-6})$ alkyl, aryl or aryl$(C_{1-6})$alkyl, any of which maybe optionally substituted;

$R^{11}$ is hydrogen or $(C_{1-6})$alkyl; and n is 0, 1, 2, 3 or 4;

or a pharmaceutically acceptable salt thereof;

provided that the compound is not:

a) N-(2-methyl-4-quinolinyl)-N'[3-(trifluoromethyl)phenyl] urea:

b) N-(4-methoxyphenyl)-N'-(2-methyl-4-quinolinyl)urea;

c) N-[3-(dimethylamino)phenyl]-N'-(2-methyl-4-quinolinyl)urea;

d) N-(3-methoxyphenyl)-N'-(2-methyl-4-quinolinyl)urea;

e) ethyl 3-[[[(2-methyl-4-quinolinyl)amino]carbonyl] amino]benzoate;

f) N-[3-hydroxyphenyl]-N'-(2-methyl-4-quinolinyl)urea;

g) N-[2,3-dichlorophenyl]-N'-(2-methyl-4-quinolinyl)urea;

h) N-benzo[b]thien-5-yl-N'-(2-methyl-4-quinolinyl)urea;

i) N-(1-methyl-1H-indol-5-yl)-N'-(2-methyl-4-quinolinyl) urea;

j) N-(2-methyl-4-quinolinyl)-N'-(5,6,7,8-tetrahydro-1-naphthalenyl)urea;

k) N-(2-methyl-4-quinolinyl)-N'-(3,4,5-trimethoxyphenyl) urea;

l) N-(2-methylphenyl)-N'-(2-methyl-4-quinolinyl)urea;

m) N-(4-methylphenyl)-N'-(2-methyl-4-quinolinyl)urea;

n) N-(3,5-dimethylphenyl)-N'-(2-methyl-4-quinolinyl)urea;

o) N-(4-chlorophenyl)-N'-(2-methyl-4-quinolinyl)urea;

p) N-(2-methyl-4-quinolinyl)-N'-[3-(trifluoromethyl) phenyl)urea;

q) N-(2-methoxyphenyl)-N'-(2-methyl-4-quinolinyl)urea;

r) N-(2-methyl-4-quinolinyl)-N'-phenylurea;

s) N-(3,4-dimethylphenyl)-N'-(2-methyl-4-quinolinyl)urea;

t) N-(4-methyl-2-nitrophenyl)-N'-(2-methyl-4-quinolinyl) urea;

u) N-(3-chloro-4-methylphenyl)-N'-(2-methyl-4-quinolinyl) urea;

v) N-(5-chloro-2-methoxyphenyl)-N'-(2-methyl-4-quinolinyl)urea;

w) 1-(6-amino-2-methyl-4-quinolinyl)-3-(o-nitrophenyl) urea; or x) N-(1,2-dihydro-6-methyl-2-oxo-4-quinolinyl)-N'-phenylthiourea.

In formula (I) Z is preferably oxygen.

When a halogen atom is present in the compound of formula (I) this may be fluorine, chlorine, bromine or iodine.

n is preferably 1 or 2, more preferably 2.

When n is 1, the group $R^1$ is preferably in the 6- or 8-position, particularly the 8-position.

When n is 2, the groups $R^1$ are preferably in the 5,8- or 6,8-positions, particularly the 5,8-positions.

$R^1$ is preferably halogen e.g. fluoro, or $(C_{1-6})$alkoxy e.g. methoxy. $R^1$ is most preferably fluoro.

When any one of $R^1$ to $R^{11}$ comprise a $(C_{1-6})$alkyl group, whether alone or forming part of a larger group, e.g. alkoxy or alkylthio, the alkyl group may be straight chain, branched or cyclic, or combinations thereof, it preferably contains 1 to 4 carbon atoms, and is most preferably methyl or ethyl.

When any one of $R^1$ to $R^{10}$ comprise a $(C_{2-6})$alkenyl group, whether alone or forming part of a larger group, the alkenyl group may be straight chain, branched or cyclic, or combinations thereof, it preferably contains 2 to 4 carbon atoms and is most preferably allyl.

Suitable optional substituents for $(C_{1-6})$alkyl, $(C_{2-6})$alkenyl, $(C_{1-6})$alkoxy and $(C_{1-6})$alkylthio groups include one or more substituents selected from halogen e.g. fluoro, $(C_{1-4})$alkoxy e.g. methoxy, hydroxy, carboxy and $(C_{1-6})$alkyl esters and $(C_{1-6})$alkylamides thereof, amino, mono- or di-$(C_{1-6})$alkylamino, $N(R^{11})COR^8$, $N(R^{11})SO_2R^8$, $CONR^9R^{10}$ and cyano. For example one or more substituents selected from halogen e.g. fluoro, $(C_{1-4})$alkoxy e.g. methoxy, hydroxy, carboxy and $(C_{1-6})$alkyl esters thereof, amino, mono- or di-$(C_{1-6})$alkylamino and cyano.

When used herein the term "aryl", whether alone or forming part of a larger group, includes optionally substituted aryl groups such as phenyl and naphthyl, preferably phenyl. The aryl group may contain up to 5, more preferably 1, 2 or 3 optional substituents. Suitable substituents for aryl groups include halogen, $(C_{1-6})$alkyl e.g. methyl, $(C_{1-6})$haloalkyl e.g. trifluoromethyl, $(C_{1-6})$alkoxy e.g. methoxy, $(C_{1-6})$alkoxy$(C_{1-6})$alkyl e.g. methoxymethyl, hydroxy, =O, carboxy and $(C_{1-6})$alkyl esters and $(C_{1-6})$mono and dialkylamides thereof, nitro, arylsulfonyl e.g. p-toluenesulfonyl, $(C_{1-6})$alkylsulfonyl e.g. methanesulfonyl, aryl$(C_{1-6})$alkyl e.g. benzyl or 3-phenylpropyl, aryl e.g. phenyl, hydroxy$(C_{1-6})$alkyl e.g. hydroxyethyl, $R^aCO_2$—, $R^aCO_2(C_{1-6})$alkyl e.g. carboethoxypropyl, cyano, cyano$(C_{1-6})$alkyl e.g. 3-cyanopropyl, $R^aR^bN$, $R^aR^bN(C_{1-6})$alkyl, $R^aR^bNCO(C_{1-6})$alkyl in which $R^a$ and $R^b$ are independently selected from hydrogen and $(C_{1-6})$alkyl.

When any one of $R^2$ to $R^6$, $R^8$, $R^9$ or $R^{10}$ represent heterocyclyl or heterocyclyl$(C_{1-6})$alkyl the heterocyclyl group is preferably a 5- to 10-membered monocyclic or bicyclic ring, which may be saturated or unsaturated, for example containing 1, 2 or 3 heteroatoms selected from oxygen, nitrogen and sulfur; for example pyrrolidine, oxazole, morpholinc, pyrimidine or phthalimide. A ring containing one or two nitrogen atoms is especially preferred. The heterocyclyl group may contain up to 5, more preferably 1, 2 or 3 optional substituents. Suitable substituents for heterocyclyl groups include those mentioned above for aryl groups.

When an adjacent pair of $R^2$ to $R^6$ together with the carbon atoms to which they are attached form a carbocyclic or heterocyclic ring this is preferably a 5- to 7-membered ring, which may be aromatic or non-aromatic. Heterocyclic rings preferably contain 1, 2 or 3 heteroatoms selected from oxygen, nitrogen and sulfur; for example oxazole, imidazole, thiophene, pyran, dioxan, pyrrole or pyrrolidine. A ring containing one nitrogen atom and one oxygen atom is preferred. It is particularly preferred for the nitrogen to be attached directly to the $R^4$ position. A carbocyclic or heterocyclic ring formed by an adjacent pair of $R^2$ to $R^6$ together with the carbon atoms to which they are attached may be optionally substituted on carbon or nitrogen by one or more substituents, e.g. up to 3 substituents. Suitable substituents for the carbocyclic or heterocyclic ring include those mentioned above for aryl groups.

A preferred group of compounds are those in which $R^2$ to $R^6$ independently represent hydrogen, $R^8CO$—, $NR^9R^{10}CO$— wherein $R^9$ is preferably represents hydrogen and $R^{10}$ preferably represents $(C_{1-6})$alkyl, halogen, $(C_{1-6})$alkoxy e.g. methoxy, $(C_{1-6})$alkylthio e.g. methylthio, or $NR^9R^{10}$ wherein $R^9$ and $R^{10}$ preferably represent $(C_{1-6})$alkyl e.g. dimethylamino, and at least one of $R^2$ to $R^6$ is other than hydrogen; or an adjacent pair of $R^2$ to $R^6$ together with the carbon atoms to which they are attached form an optionally substituted 5- to 7-membered carbocyclic or heterocyclic ring, e.g. a 6- or 7-membered non-aromatic heterocyclic ring, a 5- or 6membered non-aromatic carbocyclic ring or a 5- or 6-membered aromatic heterocyclic ring.

A further preferred group of compounds are those in which $R^2$, $R^5$ and $R^6$ represent hydrogen.

A further preferred group of compounds are those in which $R^2$, $R^4$ and $R^6$ represent hydrogen.

A preferred group of compounds are those in which either $R^3$ and $R^4$, or $R^3$ and $R^5$ are other than hydrogen.

A group of compounds which may be mentioned are the compounds of formula (Ia):

(Ia)

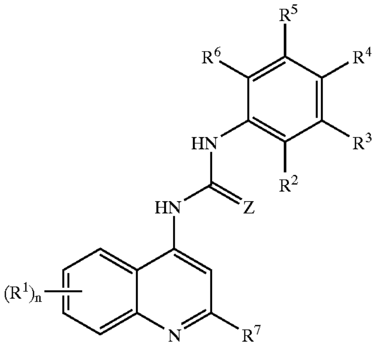

in which:

Z represents oxygen or sulfur;

$R^1$ represents $(C_{1-6})$alkyl, $(C_{2-6})$alkenyl or $(C_{1-6})$alkoxy, any of which may be optionally substituted; halogen, $R^8CO$— or $NR^9R^{10}CO$—;

$R^2$, $R^3$, $R^4$, $R^5$ and $R^6$ independently represent $(C_{1-6})$alkyl, $(C_{2-6})$alkenyl, $(C_{1-6})$ alkoxy or $(C_{1-6})$alkylthio, any of which may be optionally substituted; hydrogen, halogen, nitro, cyano, aryloxy, aryl$(C_{1-6})$alkyloxy, aryl$(C_{1-6})$alkyl, $R^8CO$—, $R^8SO_2NH$—, $R^8CON(R^{11})$—, $NR^9R^{10}$—, $NR^9R^{10}CO$—, —$COOR^9$, heterocyclyl or heterocyclyl$(C_{1-6})$alkyl;

or an adjacent pair of $R^2$, $R^3$, $R^4$, $R^5$ and $R^6$ together with the carbon atoms to which they are attached form an optionally substituted carbocyclic or heterocyclic ring;

$R^7$ is $(C_{1-6})$alkyl, $(C_{2-6})$alkenyl, $(C_{1-6})$alkoxy or $(C_{1-6})$alkylthio, any of which may be optionally substituted; halogen, hydroxy, nitro, cyano, $NR^9R^{10}$—, $NR^9R^{10}CO$—, $N_3$, —$OCOR^9$ or $R^8CON(R^{11})$—;

$R^8$ is $(C_{1-6})$alkyl or aryl;

$R^9$ and $R^{10}$ independently represent hydrogen; $(C_{1-6})$alkyl, aryl or aryl$(C_{1-6})$alkyl;

$R^{11}$ is hydrogen or $(C_{1-6})$alkyl; and n is 0, 1, 2 or 3;

or a pharmaceutically acceptable salt thereof;
provided that the compound is not:

a) N-(2-methyl-4-quinolinyl)-N'-[3-(trifluoromethyl)phenyl]urea;

b) N-(4-methoxy)-N'-(2-methyl-4-quinolinyl)urea;

c) N-[3-(dimethylamino)phenyl]-N'-(2-methyl-4-quinolinyl)urea;
d) N-(3-methoxyphenyl)-N'-(2-methyl-4-quinolinyl)urea;
e) Ethyl 3-[[[(2-methyl-4-quinolinyl)amino]carbonyl]amino]benzoate;
f) N-[3-hydroxyphenyl]-N'-(2-methyl-4-quinolinyl)urea;
g) N-[2,3-dichlorophenyl]-N'-(2-methyl-4-quinolinyl)urea;
h) N-benzo[b]thien-5-yl-N'-(2-methyl-4-quinolinyl)urea;
i) N-(1-methyl-1H-indol-5-yl)-N'-(2-methyl-4-quinolinyl)urea;
j) N-(2-methyl-4-quinolinyl)-N'-(5,6,7,8-tetrahydro-1-naphthalenyl)urea;
k) N-(2-methyl-4-quinolinyl)-N'-(3,4,5-trimethoxyphenyl)urea;
l) N-(2-methylphenyl)-N'-(2-methyl-4-quinolinyl)urea;
m) N-(4-methylphenyl)-N'-(2-methyl-4-quinolinyl)urea;
n) N-(3,5-dimethylphenyl)-N'-(2-methyl-4-quinolinyl)urea;
o) N-(4-chlorophenyl)-N'-(2-methyl-4-quinolinyl)urea;
p) N-(2-methyl-4-quinolinyl)-N'-[3-(trifluoromethyl)phenyl)urea;
q) N-(2-methoxyphenyl)-N'-(2-methyl-4-quinolinyl)urea;
r) N-(2-methyl-4-quinolinyl)-N'-phenylurea;
s) N-(3,4-dimethylphenyl)-N'-(2-methyl-4-quinolinyl)urea;
t) N-(4-methyl-2-nitrophenyl)-N'-(2-methyl-4-quinolinyl)urea;
u) N-(3-chloro-4-methylphenyl)-N'-(2-methyl-4-quinolinyl)urea;
v) N-(5-chloro-2-methoxyphenyl)-N'-(2-methyl-4-quinolinyl)urea;
w) 1-(6-amino-2-methyl-4-quinolinyl)-3-(o-nitrophenyl)urea; or
x) N-(1,2-dihydro-6-methyl-2-oxo-4-quinolinyl)-N'-phenylthiourea.

In the compounds of formula (Ia) suitable substituents for aryl groups and for heterocyclyl groups when any one of $R^2$ to $R^6$ represent heterocyclyl or heterocyclyl($C_{1-6}$)alkyl include halogen, ($C_{1-4}$)alkyl e.g. methyl, ($C_{1-4}$)haloalkyl e.g. trifluoromethyl, ($C_{1-4}$)alkoxy e.g. methoxy, ($C_{1-4}$)alkoxy($C_{1-4}$)alkyl e.g. methoxymethyl, hydroxy, carboxy and ($C_{1-6}$)alkyl esters, amino, nitro, arylsulfonyl e.g. p-toluenesulfonyl, and ($C_{1-4}$)alkylsulfonyl e.g. methanesulfonyl. Suitable substituents for carbocyclic or heterocyclic rings when an adjacent pair of $R^2$ to $R^6$ together with the carbon atoms to which they are attached form carbocyclic or heterocyclic ring include ($C_{1-4}$)alkyl e.g. methyl, ($C_{1-4}$)alkoxy, ($C_{1-4}$)alkoxy($C_{1-4}$)alkyl e.g. methoxymethyl, hydroxy, =O, aryl($C_{1-4}$)alkyl e.g. benzyl or 3-phenylpropyl, aryl e.g. phenyl, hydroxy($C_{1-4}$)alkyl e.g. hydroxyethyl, $R^aCO_2$—, $R^aCO_2$ ($C_{1-4}$)alkyl e.g. carboethoxypropyl, cyano, cyano($C_{1-4}$)alkyl e.g. 3-cyanopropyl, $R^aR^bN$ and $R^aR^bN$($C_{1-4}$)alkyl in which $R^a$ and $R^b$ are independently selected from hydrogen and ($C_{1-4}$)alkyl.

A further group of compounds of formula (Ia) are those in which $R^2$ to $R^6$ independently represent hydrogen, halogen, ($C_{1-6}$)alkoxy e.g. methoxy, ($C_{1-6}$)alkylthio e.g. methylthio, or $NR^9R^{10}$ wherein $R^9$ and $R^{10}$ preferably represent ($C_{1-6}$)alkyl e.g. dimethylamino, and at least one of $R^2$ to $R^6$ is other than hydrogen; or an adjacent pair of $R^2$ to $R^6$ together with the carbon atoms to which they are attached form an optionally substituted 5- to 7-membered heterocyclic ring, e.g. a 6- or 7-membered non-aromatic heterocyclic ring or a 5- or 6-membered aromatic heterocyclic ring.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature the invention provides a process for the preparation of the compounds of formula (I) and salts thereof which comprises coupling a compound of formula (II):

(II)

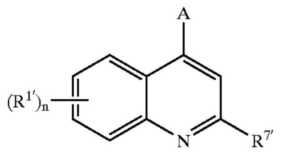

with a compound of formula (III):

(III)

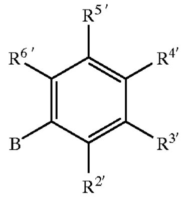

wherein A and B are appropriate functional groups to form the —NHCONH— or —NHCSNH— moiety when coupled; n is as defined in formula (I); and $R^{1'}$ to $R^{7'}$ are $R^1$ to $R^7$ as defined in formula (I) or groups convertible thereto; and thereafter optionally and as necessary and in any appropriate order, converting any $R^{1'}$ to $R^{7'}$ when other than $R^1$ to $R^7$ respectively to $R^1$ to $R^7$, and/or forming a pharmaceutically acceptable salt thereof. Suitable examples of groups A and B are:

(i) A and B are —$NH_2$ (ii) one of A and B is —$CON_3$ and the other is —$NH_2$ (iii) one of A and B is —$CO_2H$ and the other is —$NH_2$ (iv) one of A and B is —N═C═O and the other is —$NH_2$ (v) one of A and B is —N═C═S and the other is —$NH_2$ (vi) one of A and B is —NHCOL and the other is —$NH_2$ (vii) one of A and B is halogen and the other is —$NHCONH_2$ (viii) one of A and B is $NHCOCBr_3$ and the other is $NH_2$ Wherein L is a leaving group such as chloro or bromo, imidazole or phenoxy or phenylthio optionally substituted for example with halogen, for example chlorine.

When A and B are both —$NH_2$, the reaction is generally effected in the presence of a urea coupling agent such as 1,1'-carbonyldiimidazole or triphosgene.

When one of A and B is —$CO_2H$ and the other is —$NH_2$ the reaction is generally effected in the presence of an agent such as diphenylphosphoryl azide and ill the presence of a base such as triethylamine.

When one of A and B is —N═C═O or —N═C═S and the other is —$NH_2$ the reaction is suitably carried out in an inert solvent for example dimethylformamide or dichloromethane and/or toluene at ambient or elevated temperature, preferably ambient.

When one of A and B is —$CON_3$ or —$CO_2H$ and the other is —$NH_2$ the reaction is suitably carried out in an inert solvent for example toluene or dimethylformamide at elevated temperature.

Where one of A and B is —NHCOL and the other is —$NH_2$, the reaction is suitably carried out in an inert solvent such as dichloromethane at ambient temperature optionally in the presence of a base, such as triethylamine or in dimethylformamide at ambient or elevated temperature.

When one of A and B is halogen and the other is —$NHCONH_2$ the reaction is suitably carried out in an inert solvent such as toluene at elevated temperature, optionally in the presence of base.

When one of A and B is —$NHCOCBr_3$ and the other is $NH_2$ the reaction is suitably carried out in an inert solvent such as dimethylsulfoxide or pyridine at elevated temperatures in the presence of a base such as DBU.

Suitable examples of compounds having groups $R^{1'}$ to $R^{7'}$ which are convertible to $R^{1'}$ to $R^{7'}$ respectively include compounds where one or more of $R^{2'}$ to $R^{7'}$ are OH or $NH_2$; and compounds where an adjacent pair of $R^{2'}$ to $R^{6'}$ together with the carbon atoms to which they are attached represent a fused pyrrole ring which is unsubstituted on nitrogen, where treatment with a base, e.g. sodium hydride, and reaction with an electrophile, e.g. methyl iodide, benzyl chloride or benzenesulfonyl chloride, affords the corresponding substituent on the pyrrole nitrogen.

Compounds of formula (II) and (III) where A or B is —$NH_2$, —N═C═S or halogen are known compounds or can be prepared analogously to known compounds.

Compounds of formula (II) and (III) where A or B is —N═C═O may be prepared by treating a compound of formula (II) or (III) in which:

(i) A or B is —$NH_2$, with phosgene or a phosgene equivalent, in the presence of excess base or an inert solvent.

(ii) A or B is —$CON_3$, via the nitrene, by thermal rearrangement using conventional conditions (L. S. Trifonov et al, *Helv. Chim. Acta,* 1987, 70, 262).

(iii) A or B is —$CONH_2$, via the nitrene intermediate using conventional conditions.

Compounds of formula (II) and (III) where A or B is —NHCOL may be prepared by reacting a compound of formula (II) or (III) in which A or B is —$NH_2$ with phosgene or a phosgene equivalent, in an inert solvent, at low temperature, if necessary in the presence of a base such as triethylamine. Examples of phosgene equivalents include triphosgene, 1,1'-carbonyldiimidazole, phenyl chloroformate and phenyl chlorothioformate.

Compounds of formula (II) and (III) where A or B is —$NHCONH_2$ can be prepared from compounds of formula (II) or (III) where A or B is —$NH_2$ by reaction with an inorganic isocyanate under conventional conditions.

Compounds of formula (II) and (III) where A or B is —$NHCOCBr_3$ can be prepared from compounds of formula (II) or (III) where A or B is —$NH_2$ by reaction with tribromoacetyl chloride in an inert solvent such as dichloromethane in the presence of a base such as triethylamine.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Novel intermediates of formulae (II) and (III) are also part of this invention.

According to a further feature the invention provides a compound of formula (II):

(II)

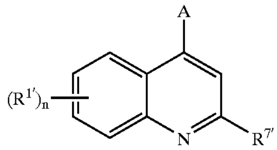

wherein A is —$NH_2$, —$CON_3$, —$NH_2$, —$CO_2H$, —N═C═O, —N═C═S, —NHCOL, halogen or —$NHCOCBr_3$, L is a leaving group, n is as defined in formula (I) and $R^1$ and $R^7$ are $R^{1'}$ and $R^{7'}$ as defined in formula (I) or groups convertible thereto.

Pharmaceutically acceptable salts may be prepared conventionally by reaction with the appropriate acid or acid derivative.

As indicated above the compounds of formula (I) and their pharmaceutically acceptable salts, without provisos a)–x), are useful for the treatment of diseases or disorders where an antagonist of a human orexin receptor is required especially feeding disorders, such as obesity and diabetes; prolactinoma; hypoprolactinemia, hypothalamic disorders of growth hormone deficiency; idiopathic growth hormone deficiency; Cushings syndrome/disease: hypothalainic-adrenal dysfunction; dwarfism; sleep disorders; sleep apnea; narcolepsy; insomnia; parasomnia; jet-lag syndrome; and sleep disturbances associated with such diseases as neurological disorders, neuropathic pain, restless leg syndrome, heart and lung diseases, mental illness such as depression or schizophrenia, and addictions; sexual dysfunction; psychosexual dysfunction; sex disorder; sexual disorder; bulimia; and hypopituitarism.

The compounds of formula (I) and their pharmaceutically acceptable salts, without provisos a)–x), are particularly useful for the treatment of obesity, including obesity associated with Type 2 diabetes, and sleep disorders.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The present invention also provides a method of treating or preventing diseases or disorders where an antagonist of a human orexin receptor is required, which comprises administering to a subject in need thereof an effective amount of a compound of formula (I), or a pharmaceutically acceptable salt thereof, without provisos a)–x).

The present invention also provides a compound of formula (I), or a pharmaceutically acceptable salt thereof, without provisos a)–x), for use in the treatment or prophylaxis of diseases or disorders where an antagonist of a human orexin receptor is required.

The present invention also provides the use of a compound of formula (I), or a pharmaceutically acceptable salt thereof, without provisos a)–x), in the manufacture of a medicament for the treatment or prophylaxis of diseases or disorders where an antagonist of a human orexin receptor is required.

For use in medicine, the compounds of the present invention are usually administered as a pharmaceutical composition. The present invention also provides a pharmaceutical composition comprising a compound of formula (I), or a pharmaceutically acceptable salt thereof, and a pharmaceutically acceptable carrier.

The compounds of formula (I) and their pharmaceutically acceptable salts, without provisos a)–x), may be administered by any convenient method, for example by oral, parenteral, buccal, sublingual, nasal, rectal or transdermal administration and the pharmaceutical compositions adapted accordingly.

The compounds of formula (I) and their pharmaceutically acceptable salts, without provisos a)–x), which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon or hydrofluorocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable salt thereof, without provisos a)–x). used in the treatment or prophylaxis of the abovementioned disorders or diseases will vary in the usual way with the particular disorder or disease being treated, the weight of the subject and other similar factors. However as a general rule suitable unit doses may be 0.05 to 1000 mg, more suitably 0.05 to 500 mg; such unit doses may be administered more than once a day for example two or three times a day, so that the total daily dosage is in the range of about 0.01 to 100 mg/kg; and such therapy may extend for a number of weeks or months. In the case of physiologically acceptable salts the above figures are calculated as the parent compound of formula (I), without provisos a)–x).

No toxicological effects are indicated/expected when a compound of formula (I), without provisos a)–x), is administered in the above mentioned dosage range.

Human orexin-A referred to above has the amino acid sequence:

```
pyroGlu Pro Leu Pro Asp Cys Cys Arg Gln Lys Thr Cys Ser Cys Arg Leu
 1              5                   10                  15

Tyr Glu Leu Leu His Gly Ala Gly Asn His Ala Ala Gly Ile Leu Thr
            20                  25                  30

Leu-NH2
```

Orexin-A can be employed in a process for screening for compounds (antagonists) which inhibit the ligand's activation of the orexin-1 receptor.

In general, such screening procedures involve providing appropriate cells which express the orexin-1 receptor on the surface thereof. Such cells include cells from mammals, yeast, Drosophila or *E. coli*. In particular, a polynucleotide encoding the orexin-1 receptor is employed to transfect cells to thereby express the receptor. The expressed receptor is then contacted with a test compound and an orexin-1 receptor ligand to observe inhibition of a functional response.

One such screening procedure involves the use of melanophores which are transfected to express the orexin-1 receptor. Such a screening technique is described in WO 92/01810.

Another such screening technique involves introducing RNA encoding the orexin-1 receptor into Xetoptis oocytes to transiently express the receptor. The receptor oocytes may then be contacted with a receptor ligand and a compound to be screened, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on the surface thereof. Such a method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand can be labelled, e.g. by radioactivity. The amount of labelled ligand bound to the receptors is measured, e.g. by measuring radioactivity of the receptors. If the compound binds to the receptor as determined by a reduction of labelled ligand which binds to the receptors, the binding of labelled ligand to the receptor is inhibited.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor. The ligand used in the screening method described below to determine the antagonist activity of compounds according to the invention is orexin-A which has the amino acid sequence shown above.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. In the Examples $^1H$ NMR's were measured at 250 MHz in $d_6$-DMSO unless otherwise stated. All hydrochloride salts unless otherwise stated were prepared by dissolving/suspending the free-base in methanol and treating with an excess of ethereal HCl (1M).

Description 1

4-Amino-5,8-difluoro-2-methylquinoline (D1)

Step 1

4-Hydroxy-5,8-difluoro-2-methylquinoline

A mixture of 2,5-difluoroaniline (7.5 ml) and ethyl acetoacetate (9.6 ml) were combined in toluene (15 ml) containing acetic acid (1.5 ml). The mixture was boiled under Dean-Stark azeotrope conditions, cooled and solvent removed at reduced pressure to give crude (E)-3-(2,5-difluoro-phenylamino)-but-2-enoic acid ethyl ester (16.17 g). (E)-3-(2,5-Difluoro-phenylamino)-but-2-enoic acid ethyl ester (2 g) was refluxed in Dowtherm-A (40 ml) for 3 h. After cooling the Dowtherm was diluted with pentane (40 ml) and the precipitated title compound isolated by filtration. (Method A). $^1H$ NMR δ: 2.34 (3H, s), 5.91 (1H, s), 6.96 (1H, m), 7.53 (1H, m), 11.48 (1H, brs).

OR

A mixture of 2,5-difluoroaniline (10.0 g), ethyl acetoaceate (9.85 ml) and polyphosphoric acid (62 ml) were heated with stirring at 180° C. for 5 h. The mixture was cooled to room temperature and neutralised with dilute $NH_4OH$/ice. The title compound precipitated and was separated by filtration to give compound identical spectroscopically with a sample prepared by the two stage process described above.

Step 2

4-Chloro-5,8-difluoro-2-methylquinoline

4-Hydroxy-5,8-difluoro-2-methylquinoline (5.4 g) in phosphoryl chloride (60 ml) was boiled for 4 h. The mixture was cooled to room temperature, excess phosphoryl chloride removed at reduced pressure, the residue dissolved in ethyl acetate, washed with sodium hydrogen carbonate, dried ($Na_2SO_4$) and solvent removed at reduced pressure. The title compound (5.35 g) was isolated as a brown powder. (Method B). $^1H$ NMR δ: 2.61 (3H, s), 7.46 (1H, m), 7.66 (1H, m), 7.81 (1H, s).

Step 3

4-Azido-5,8-difluoro-2-methylquinoline

4-Chloro-5,8-difluoro-2-methylquinoline (8.18 g) in dimethylformamide (80 ml) was treated with sodium azide (3.7 g) and the mixture heated for 20 h. The mixture was cooled, poured into ice/water and extracted with dichloromethane (2×200 ml). The organic phase was washed with water, dried ($Na_2SO_4$) and solvent removed at reduced pressure. The residue was column chromatographed (silica gel (5–20% diethyl ether in pentane) to give the title compound (5.45 g) as a colourless solid. (Method C). $^1H$ NMR δ: 2.67 (3H, s), 7.29 (1H, m), 7.54 (1H, s), 7.58(1H, m).

Step 4

4-Amino-5,8-difluoro-2-methylquinoline

4-Azido-5 ,8-difluoro-2-methylquinoline (0.55 g) was suspended in methanol (20 ml) and sodium borohydride (200 mg) added. After 1 h additional sodium borohydride (0.4 g) was added and stirring continued for a further 3 h. Solvent was removed at reduced pressure and the residue dissolved in 2N HCl (10 ml). Excess sodium hydroxide was added and the title compound (0.44 g) collected by filtration as a yellow solid. (Method D). $^1H$ NMR ($CDCl_3$) δ: 2.60 (3H, s), 5.28 (2H, brs), 6.47 (1H, s), 6.90 (1H, m), 7.19 (1H, m), 7.26 (1H, s).

Descriptions 2–10 were prepared by standard methods illustrated by Description 1 using an appropriately substituted aniline (using steps 1–4 of D1) or where commercially available a 4-hydroxy-(using steps 2–4 of D1) or 4chloro-quinoline (using steps 3–4 of D1).

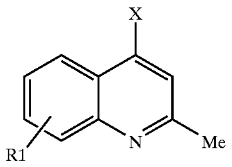

| Compound | $R^1$ | X | method | yield | NMR/MS ($API^+$) |
|---|---|---|---|---|---|
| Description 2: 4-Amino-6,8-difluoro-2-methylquinoline (D2) | | | | | |
| 4-Hydroxy-6,8-difluoro-2-methylquinoline is commercially available from Maybridge | | | | | |
| D2 (step 2) | 6,8-diF | Cl | B | 81% | $^1H$ NMR ($CDCl_3$) δ: 2.59(3H, s), 7.70(1H, m), 7.85(2H, m) |
| D2 (step 3) | 6,8-diF | $N_3$ | C | 74% | $^1H$ NMR ($CDCl_3$) δ: 2.67(3H, s), 7.46(1H, m), 7.54(1H, s), 7.75(1H, m) |
| D2 (step 4) | 6,8-diF | $NH_2$ | D | 76% | $^1H$ NMR ($CDCl_3$) δ: 2.42(3H, s), 6.51(1H, s), 6.79(2H, brs), 7.48(1H, m), 7.76(1H, m) |
| Description 3: 4-Amino-8-fluoro-2-methylquinoline (D3) | | | | | |
| 4-Chloro-8-fluoro-2-methylquinoline is commercially available from Ubichem | | | | | |
| D3 (step 3) | 8-F | $N_3$ | C | 89% | $^1H$ NMR δ: 2.68(3H, s), 7.49(1H, s), 7.47–7.70(m, 2H), 7.76(1H, d, J=7.0Hz) |
| D3 (step 4) | 8-F | $NH_2$ | D | 80% | $^1H$ NMR δ: 2.43(3H, s), 6.49(1H, s), 6.79(2H, brs), 7.22–7.40(2H, m), 7.89(1H, d, J=8.2Hz) |
| Description 4: 4-Amino-5,6-difluoro-2-methylquinoline (D4) | | | | | |
| D4 (step 1) | 5,6-diF | OH | A | 76* | contains 80% of 6,7-difluororegioisomer 196 |
| D4 (step 2) | 5,6-diF | Cl | B | 7.4% | 214, 216 |
| D4 (step 3) | 5,6-diF | $N_3$ | C | 96% | $^1H$ NMR ($CDCl_3$) δ: 2.72(3H, s), 7.07(1H, s), 7.48–7.59(1H, m), 7.73–7.79(1H, m) |
| D4 (step 4) | 5,6-diF | $NH_2$ | D | 86% | 195 $MH^+$ |
| Description 5: 4-Amino-5,7-difluoro-2-methylquinoline (D5) | | | | | |
| D5 (step 1) | 5,7-diF | OH | A | 47% | 196 $MH^+$ |
| D5 (step 2) | 5,7-diF | Cl | B | 92% | 214, 216 $MH^+$ |
| D5 (step 3) | 5,7-diF | $N_3$ | C | 55% | 193 (M + H − 28) |
| D5 (step 4) | 5.7-diF | $NH_2$ | D | 85% | 195 $MH^+$ |
| Description 6: -4-Amino-6-chloro-2-methylquinoline (D6) | | | | | |
| D4, 6-dichloro-2-methylquinoline is commercially available from Ubichem | | | | | |
| D6 (step 3) | 6-Cl | $N_3$ | C | 95% | 191, 193 (M + H − 28) |
| D6 (step 4) | 6-Cl | $NH_2$ | D | 92% | 193, 195 $MH^+$ |
| Description 7: 4-Amino-7,8-difluoro-2-methylquinoline (D7) | | | | | |
| D7 (step 1) | 7,8-diF | OH | A | 35% | $^1H$ NMR δ: 2.37(3H, s), 5.97(1H, s), 7.28–7.38(1H,m), 7.84–7.90(1H, m), 11.70(1H, brs) |
| D7 (step 2) | 7,8-diF | Cl | B | 83% | 214, 216 $MH^+$ |

-continued

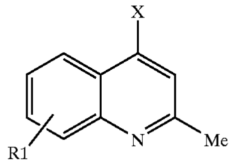

| Compound | $R^1$ | X | method | yield | NMR/MS ($API^+$) |
|---|---|---|---|---|---|
| D7 (step 3) | 7,8-diF | $N_3$ | C | 87% | 193 (M + H − 28) |
| D7 (step 4) | 7,8-diF | $NH_2$ | D | 77% | 195 $MH^+$ |
| Description 8: 4-Amino-6-fluoro-2-methylquinoline (D8) | | | | | |
| D4-Chloro-6-fluoro-2-methylquinoline is commercially available from Ubichem | | | | | |
| D8 (step 3) | 6-F | $N_3$ | | 87% | 175 (M + H − 28) |
| D8 (step 4) | 6-F | $NH_2$ | | 98% | 177 $MH^+$ |
| Description 9: 4-Amino-8-bromo-2methylquinoline (D9) | | | | | |
| D8-Bromo-4-chloro-2-methylquinoline is commercially available from Ubichem | | | | | |
| D9 (step 3) | 8-Br | $N_3$ | C | 74% | 234, 236 (M + H − 28) |
| D9 (step 4) | 8-Br | $NH_2$ | D | 97% | 238 $MH^+$ |
| Description 10: 4-Amino-8-chloro-2,7-dimethylquinoline (D10) | | | | | |
| D10 (step 1) | 8-Cl, 7-Me | OH | A | 38% | $^1$H NMR($CDCl_3$) δ: 2.46(3H, s), 2.52(3H, s), 7.15(1H, s), 7.20(1H, d, J=8.5Hz), 8.14(1H, d, J=8.5Hz), 8.36(1H, brs) |
| D10 (step 2) | 8-Cl, 7-Me | Cl | B | 95% | $^1$H NMR ($CDCl_3$) δ: 2.64(3H, s), 2.73(3H, s), 7.41(1H, s), 7.45(1H, d, J=8.5Hz), 8.01(1H, d, J=8.5Hz) |
| D10 (step 3) | 8-Cl, 7-Me | $N_3$ | C | 63% | $^1$H NMR ($CDCl_3$) δ: 2.62(3H, s), 2.80(3H, s), 7.03(1H, s), 7.33(1H, d, J=8.5Hz), 7.82(1H, d, J=8.5Hz) |
| D10 (step 4) | 8-Cl, 7-Me | $NH_2$ | | 94% | $^1$H NMR δ: 2.43(3H, s), 2.51(3H, s), 6.45(1H, s), 6.75(2H, brs), 7.27(1H, d, J=8.5Hz), 7.96 (1H, d, J=8.5Hz) |

$^1$H NMR and/or mass spectra were consistent with the structures in the table.

Description 11

4-Amino-2-methyl-8-vinylquinoline (D1)

A mixture of D9 (0.50 g), lithium chloride (0.265 g), tributylvinyl tin (0.73 g) and bis(triphenylphosphine) palladium(II)chloride (0.05 g) in dimethylformamide (20 ml) was heated at 100° C. for 20 h. Solvent was removed at reduced pressure, the residue dissolved in dichloromethane, filtered and solvent removed at reduced pressure. The residue was extracted with diethyl ether, the extracts evaporated to dryness and the residue column chromatographed (silica gel, 0–10% methanol [containing 1% ammonia] in dichloromethane eluant) to give the title compound (0.13 g). $^1$H NMR δ: 2.51 (3H, s), 5.39 (1H, d), 5.93 (1H, d), 6.51 (1H, s), 7.14 (2H, brs), 7.40 (1H, m), 7.76–7.91 (2H, m), 8.10 (1H, d).

Description 12

2-Methylthioquinoline-4-carboxylic acid (D12)

Step 1

2-Methylthioquinoline-4-carboxylic Acid Methyl Ester

2-Chloroquinoline-4-carboxylic acid methyl ester (0.5 g) (DE 3721222) in dimethylformamide (10 ml) was treated with sodium thiomethoxide (0.16 g) and heated at 80° C. for 2 h. Solvent was removed at reduced pressure triturated with dichloromethane and filtered through celite. Solvent was reduced to 2 ml and petroleum ether (40–60) added. The precipitated product (0.40 g) was separated by filtration to give 2-methylthioquinoline-4-carboxylic acid methyl ester. m/z ($API^+$): 234 ($MH^+$).

Step 2

2-Methylthioquinoline-4-carboxylic acid

2-Methylthioquinoline-4-carboxylic acid methyl ester (0.40 g) in methanol:2N sodium hydroxide (2:1, 45 ml) was heated at 60° C. until all solid had dissolved. Volume of solvent was reduced to (15 ml) at reduced pressure and acidified with 2N HCl (16 ml). The precipitated solid was separated by filtration and dried to give the title compound (0.39 g). $^1$H NMR δ: 2.68 (3H, s), 7.56 (1H, m), 7.75–7.80 (2H, m), 7.96 (1H, d, J=8.2 Hz), 8.55 (1H, d), 13.91 (1H, brs).

Description 13

2-Fluoroquinoline-4-carboxylic acid (D13)

Step 1

2-Fluoroquinoline-4-carboxylic Acid Methyl Ester

2-Chloroquinoline-4-carboxylic acid methyl ester (1.14 g) in dimethylsulfone (4.0 g) was treated with potassium fluoride (2.5 g) and heated at 180° C. for 1 h. The reaction mixture was cooled to room temperature, diluted with dichloromethane:water (1:1, 200 ml), the organic phase separated, solvent removed at reduced pressure and the residue column chromatographed (silica gel, dichloromethane eluant) to give 2-fluoroquinoline-4-carboxylic acid methyl ester (0.7 g). $^1$H NMR ($CDCl_3$) δ: 3.99 (3H, s), 7.57 (2H, m), 7.72 (1H, m), 7.95 (1H, d, J=8.5 Hz), 8.67 (1H, d, J=8.4 Hz). m/z ($API^+$): 205 ($MH^+$).

Step 2

2-Fluoroquinoline-4-carboxylic Acid

A solution of 2-fluoroquinoline4-carboxylic acid methyl ester (0.08 g) in dichloromethane (4 ml) was cooled to −50° C. and boron tribromide (0.08 ml) was added. After the addition of boron tribromide the reaction was warmed to room temperature and stirred for 1.5 h. The mixture was re-cooled to −50° C., quenched with water (10 ml), diluted with dichloromethane:water (1:1, 60 ml), the organic phase separated and solvent removed at reduced pressure to give 2-fluoroquinoline-4-carboxylic acid (0.02 g) after trituration with dichloromethane/petroleum ether. $^1$H NMR δ: 7.70–7.76 (2H, m), 7.85–7.96 (2H, m), 8.65 (1H, d), 14.24 (1H, brs). m/z (API−): 190 ($MH^+$).

Description 14

4-Methylthio-3-acetylbenzoic Acid (D14)

Step 1

3-Bromo-4-methylthiobenzoic Acid Methyl Ester

Sodium thiomethoxide (0.42 g) was added to a stirred solution of 3-bromo-4-fluorobenzoic acid methyl ester (10 g) in dry dimethylformamide (20 ml) and the mixture heated at 80° C. for 1 h. Solvent was removed at reduced pressure, the residue dissolved in ethyl acetate and washed with water. The organic phase was dried ($Na_2SO_4$) and solvent removed at reduced pressure to give 3-bromo-4-methylthiobenzoic acid methyl ester (0.88 g) as a colourless solid. m/z ($API^+$): 263 ($MH^+$).

Step 2

3-Acetyl-4-methylthiobenzoic Acid Methyl Ester

3-Bromo-4-methylthiobenzoic acid methyl ester (0.86 g), 1-ethoxyvinyl tributyl tin (1.39 ml) and tetrakis triphenylphosphinepalladium (IV) (0.15 g) were combined in dioxan (50 ml) and boiled for 24 h. The mixture was cooled, water (10 ml) and conc. hydrochloric acid (1 ml) added and the mixture stirred at room temperature overnight. Solvent was removed at reduced pressure, the residue dissolved in ethyl acetate and filtered through celite. The filtrate was evaporated to dryness and the residue triturated with hexane to give 3-acetyl-4-methylthiobenzoic acid methyl ester (0.45 g) as a yellow solid. m/z ($API^+$): 225 ($MH^+$).

Step 3

3-Acetyl-4-methylthiobenzoic Acid 3-acetyl4-methylthiobenzoic acid methyl ester (0.43 g) in water:methanol (1:3, 290 ml) containing sodium hydroxide (0.2 g) was stirred for 6 h. Methanol was removed at reduced pressure and the solution acidified with conc. hydrochloric acid to give 3-acetyl-4-methylthiobenzoic acid (0.32 g) after filtration. m/z ($API^+$): 211 ($MH^+$).

The compound of D14 was used to prepare Example 7.

Description 15

8-Fluoro-2-chloroquinoline-4-carboxylic acid (D15)

Step 1

8-Fluoro-2-hydroxyquinoline-4-carboxylic acid

8-Fluoroisatin (*D. Ing. Chim.* (*Brifssels*), 1982, 64(303), 3, 5–6) (13.27 g) and malonic acid were combined in acetic acid (125 ml) and boiled for 20 h. After cooling to room temperature a brown precipitate (3.3 g) was separated by filtration. Filtrate was evaporated to dryness and the resulting solid triturated with ethyl acetate/diethyl ether to give a colourless residue (1.5 g). The residual solid was compared with the material separated by filtration in ethanol (250 ml) and the mixture boiled for 16 h. Solvent volume was reduced to approximately 100 ml and the precipitated colourless solid separated by filtration giving the title compound (1.15 g). $^1$H NMR δ: 6.95 (1H, s), 7.19–7.28 (1H, m), 7.45 –7.52 (1H, m), 7.99 (1H, d J=8.3 Hz), 12.09 (1H, brs).

Step 2

8-Fluoro-2-chloroquinoline-4-carboxylic Acid

The hydroxy acid of step 1 (0.31, g) was suspended in phosphoryl chloride and the mixture boiled for 3.5 h. After cooling, the mixture was added dropwise to ice cooled water and stirred for 3 h. The precipitated product (0.267 g) was collected by filtration washed with water and dried. m/z ($API^+$): 224,226 ($MH^+$). $^1$H NMR ($CDCl_3$) δ: 7.68–7.75 (2H, m), 7.97 (1 H, s), 8.37–8.44 (1H, m), 14.15 (1H, brs).

Description 16

8-Fluoro-2-methoxyquinoline-4-carboxylic acid (D16)

Step 1

8-Fluoro-2-methoxyquinoline-4-carboxylic Acid Methyl Ester

8-Fluoro-2-chloroquinoline-4-carboxylic acid (0.986 g) suspended in dichloromethane (50 ml) was treated with dimethylformamide (3 drops) and oxalyl chloride (0.76 ml) and the mixture stirred for 2 h. Solvent was removed at reduced pressure. The residue was dissolved in methanol (50 ml) containing sodium methoxide (0.54 g) and stirred for 16 h. The solvent was removed at reduced pressure and the residue triturated with water. The precipitate was collected by filtration and column chromatographed (silica gel, 10→50% ethyl acetate/hexane) to give the title compound (0.184 g) as a colourless solid. m/z ($API^+$): 236 ($MH^+$). $^1$H NMR ($CDCl_3$) δ: 4.02 (3H, s), 4.14 (3H, s), 7.36–7.41 (2H, m), 7.49 (1H, s), 8.37 –8.41 (1H, m).

Step 2

8-Fluoro-2-methoxyquinoline-4-carboxylic Acid

8-Fluoro-2-methoxyquinoline-4-carboxylic acid methyl ester (0.1 82 g) in methanol (10 ml) containing 2N sodium hydroxide (0.41 ml) was stirred at room temperature for 16 h. Solvent was removed at reduced pressure, dissolved in water, and adjusted to pH2 with 2N hydrochloric acid. The precipitated title compound (0.155 g) was collected by filtration and dried. m/z ($API^-$): 222 ($MH^+$). $^1$H NMR δ: 4.02 (3H, s), 7.44–7.62 (3H, m), 8.31 (1H, d).

Description 17

8-Fluoro-2-methylquinoline-4-carboxylic Acid (D17)

7-Fluoroisatin (3.0 g) was added to 20% sodium hydroxide (15.6 ml) and stirred for 15 min. Stirring was continued for 3 h, solvent was removed at reduced pressure, the residue dissolved in water and acidified with 2N hydrochloric acid. The reaction was extracted with ethyl acetate (×3), the combined organic extracts dried ($Na_2SO_4$) and solvent removed at reduced pressure. The residue was triturated with diethyl ether to give the title compound (0.215 g) as a pale yellow solid. $^1$H NMR δ: 2.75 (3H, s), 7.58–7.65 (2H, m), 7.93 (1H, s), 8.41–8.51 (1H, m), 13.95 (1H, brs).

Description 18

8-Bromo-2-methylquinoline-4-carboxylic Acid (D18)

A suspension of 7-bromoisatin (6.0 g) in acetone (27 ml) was treated with sodium hydroxide (4.6 g) in water (23 ml). The mixture was heated to reflux for 8 h, cooled and solvent reduced in volume at reduced pressure to approx. 25 ml. The residual aqueous phase was acidified with conc. HCl, extracted with ethyl acetate, the organic phase dried ($MgSO_4$) and solvent removed at reduced pressure to give the title compound (7.2 g) as a yellow solid. $^1$H NMR δ: 2.85 (3H, s), 7.40 (1H, m), 7.90 (1H, s), 8.05 (1H, dd, J=1.2, 7.6 Hz), 8.79 (1H, dd, J=1.0, 8.5 Hz).

Description 19

8-Ethyl-2-methylquinoline-4-carboxylic Acid (D19)

Step 1

8-Bromo-2-methylquinoline-4-carboxylic Acid Ethyl Ester

A stirred mixture of 8-bromo-2-methylquinoline4-carboxylic acid (7.2 g), ethanol (150 ml) and conc. sulfuric acid (3 ml) was boiled for 6 h. After cooling to room temperature solvent was removed at reduced pressure, the residue treated with water and neutralised with solid potassium carbonate. The neutralised mixture was extracted with ethyl acetate, the extracts dried ($MgSO_4$) and solvent removed at reduced pressure. The residue was column chromatographed (silica gel (30% diethyl ether/60–80 petroleum ether) to give the ester (2.5 g). m/z ($API^+$): 294, 296 ($MH^+$).

Step 2

8-Ethyl-2-methylquinoline-4-carboxylic Acid Ethyl Ester

8-Bromo-2-methylquinoline4-carboxylic acid ethyl ester (0.5 g), lithium chloride (0.216 g), tetraethyltin (0.435 g) and bis(triphenylphosphine)palladium (II) chloride (0.05 g) were combined in dimethylformamide (20 ml) and heated at 100° C. for 24 h. Solvent was removed at reduced pressure, the residue dissolved in dichloromethane and filtered. Solvent was removed at reduced pressure and the residue column chromatographed (silica gel, 5% diethyl ether/pentane) to give the title compound (0.215 g). m/z ($API^+$): 244 ($MH^+$).

Step 3

8-Ethyl-2-methylquinoline-4-carboxylic Acid

8-Ethyl-2-methylquinoline-4-carboxylic acid ethyl ester (0.205 g) and 5N HCl combined and the solution boiled for 7 h. Solvent was removed at reduced pressure to give the title compound (0.195 g) as a yellow solid. m/z ($API^+$): 216 ($MH^+$), 214 (API−) 214(M-H).

Description 20

2,2,2-Tribromo-N-(8-fluoro-2-methyl-quinolin-4-yl)-acetamide (D20)

Tribromoacetyl chloride (6.05 g) was added to a suspension of quinoline D3 (3.09 g) and triethylamine (2.63 ml) in dichloromethane (175 ml). After 30 mln the mixture was washed with water (×2) and brine dried ($Na_2SO_4$) and solvent removed at reduced pressure to give the title compound (7.85 g), after trituration with diethyl ether/pentane, as an orange/yellow solid. $^1$H NMR ($CDCl_3$) δ: 2.88 (3H, s), 7.48–7.61 (3H, m), 8.25 (1H, s).

Description 21

5-Amino-2-(4-methoxy-phenoxy)-benzoic Acid Methyl Ester (D21)

Step 1

2-(4-Methoxy-phenoxy)-5-nitro-benzoic Acid Methyl Ester 2-(4-Methoxy-phenoxy)-5-nitro-benzoic acid (2.5 g), (DE 2058295) in methanol (75 ml) containing conc. sulfuric acid (3 drops) was boiled for 16 h. Solvent was removed at reduced pressure, the residue dissolved in ethyl acetate and washed with aqueous sodium hydrogen carbonate. The organic phase was dried ($Na_2SO_4$) and solvent removed at reduced pressure to give 2-(4-methoxy-phenoxy)-5-nitro-benzoic acid methyl ester (2.50 g). m/z ($API^+$): 304 ($MH^+$).

Step 2

5-Amino-2-(4-methoxy-phenoxy)-benzoic Acid Methyl Ester

The compound of step 1 (2.3 g) in methanol (150 ml) containing 10% Pd/C (0.5 g) was hydrogenated under one atmosphere of hydrogen for 18 h. The mixture was filtered (kieselguhr) and solvent removed from the filtrate under reduced pressure to give the title compound (2.0 g) as a yellow oil. $^1$H NMR ($CDCl_3$) δ: 3.69 (2H, brs), 3.77 (6H, s), 6.76–6.87 (6H, m), 7.19 (1H, d, J=2.5 Hz).

This compound was used to prepare Example 67

Description 22

2,2,2-Tribromo-N-(6,8-difluoro-2-methyl-quinolin-4-yl)-acetamide (D22)

The title compound (1.66 g) was prepared from quinoline D2 (0.75 g) and tribromoacetyl chloride according to the method of D20. $^1$H NMR ($CDCl_3$) δ: 3.08 (3H, s), 7.43–7.51 (2H, m), 8.37 (1H, s).

Description 23

2,2,2-Tribromo-N-(5,8-difluoro-2-methyl-quinolin-4-yl)-acetamide (D23)

The title compound (1.83 g) was prepared from quinoline D1 (0.75 g) and tribromoacetyl chloride (0.84 ml) according to the method of D20. $^1$H NMR ($CDCl_3$) δ: 2.82 (3H, s), 7.13–7.24 (1H, m), 7.33–7.42 (1H, m), 8.53 (1H, s).

Description 24

2,2,2-Trichloro-N-(6,8-difluoro-2-methyl-quinolin-4-yl)-acetamide (D24)

The title compound (1.83 g) was prepared from quinoline D2 (0.60 g) and trichloroacetyl chloride (0.38 ml) according to the method of D20. $^1$H NMR ($CDCl_3$) δ: 2.81 (3H, s), 7.16–7.21 (1H, m), 7.26–7.35 (1H, m), 8.15 (1H, s).

Description 25

2,2,2-Trichloro-N-(8-fluoro-2-methyl-quinolin-4-yl)-acetamide (D25)

The title compound (0.64 g) was prepared from quinoline D3 (0.35 g) and trichloroacetyl chloride (0.24 ml) according to the method of D20. $^1$H NMR ($CDCl_3$) δ: 2.83 (3H, s), 7.16–7.21 (1H, m), 7.43–7.56 (3H, m), 8.18 (1H, s).

Description 26

4-Methoxy-3-methylsulfanylmethyl-phenylamine (D26)

Step 1

1-Methoxy-2-methylsulfanylmethyl-4-nitro-benzene

Sodium thiomethoxide (0.469 g) was added to a solution of 2-methoxy-5-nitrobenzyl bromide (1.5 g) in dimethylformamide (25 ml). The mixture was stirred for 16 h, solvent removed at reduced pressure and the residue dissolved in ethyl acetate and washed with water and brine, dried ($Na_2SO_4$) and solvent removed at reduced pressure to give the title compound (1.2 g) as a yellow solid Step 2

4-Methoxy-3-methylsulfanylmethyl-phenylamine

Sodium dithionite (3.264 g) was added to a solution of 1-methoxy-2-methylsulfanylmethyl-4-nitro-benzene (0.8 g), and sodium hydrogen carbonate (1.57 g) in methanol:water (1:1, 200 ml) and stirred at room temperature for 16 h. Solvent was removed at reduced pressure, the residue partitioned between water and ethyl acetate, the organic phase separated, washed with brine dried ($Na_2SO_4$) and solvent removed at reduced pressure to give the title compound (0.23 g) as a brown oil. m/z ($API^+$): 184 ($MH^+$).

The compound D26 was used to prepare Example 80.

Description 27

5-Amino-2-ethyl-benzoic Acid Methyl Ester (D27)

Step 1

2-Ethyl-5-nitrobenzoic Acid Methyl Ester

2-Bromo-5-nitrobenzoic acid methyl ester (1.0 g), lithium chloride (0.49 g), tetraethyltin (0.96 g) and bis (triphenylphosphine)-palladium(II)chloride (0.1 g) were combined in dimethylformamide (20 ml) and heated at 100° C. for 8 h. Solvent was removed at reduced pressure and the residue column chromatographed (silica gel, dichloromethane/petroleum ether 30:70) to give the title compound (0.45 g). $^1$H NMR ($CDCl_3$) δ: 1.28 (3H, t, J=7.4 Hz), 3.10 (2H, q, J=7.4Hz), 3.96 (3H, s), 7.47 (1H, d, J=8.5 Hz), 8.27 (1H, dd, J=2.5, 8.5 Hz), 8.73 (1H, d, J=2.5 Hz)

Step 2

5-Amino-2-ethyl-benzoic Acid Methyl Ester

The compound of step 1 (0.45 g) in methanol (50 ml) containing 2N HCl (4 ml) was shaken under a hydrogen atmosphere (25° C., 50 psi) for 1 h. The mixture was filtered (kieselguhr), the filtrate neutralised with sodium hydroxide (4 ml, 2N) reduced to dryness, and the residue extracted with dichloromethane. The dichloromethane extracts were dried ($MgSO_4$) and solvent removed at reduced pressure to giver the title compound (0.30 g). $^1$H NMR ($CDCl_3$) δ: 1.17 (3H, t, J=7.4 Hz), 2.85 (2H, q, J=7.4Hz), 3.57 (2H, brs), 3.87 (3H, s), 6.76 (1H, dd, J=2.5, 8.5 Hz), 7.05 (1H, d, 8.5 Hz), 7.17 (1H, d, J=2.5 Hz).

Compound D27 was used to prepare Example 68.

Description 28

5-Amino-N-cyclopropylmethyl-2-ethyl-benzamide (D28)

Step 1

2-Ethyl-5-nitrobenzoic Acid

Ethyl-5-nitrobenzoic acid methyl ester (1.0 g) in methanol/2N sodium hydroxide (60 ml, 1:1) was stirred for 1 h at 60° C. Half the solvent was removed at reduced pressure, the residue diluted with water (20 ml), washed with dichloromethane and the aqueous phase acidified with 2N HCl. The acidic phase was extracted with dichloromethane, the combined extracts dried ($MgSO_4$) and solvent removed at reduced pressure to give the title compound (0.45 g) as a colourless solid. $^1$H NMR ($CDCl_3$) δ: 1.32 (3H, t, J=7.6 Hz), 3.19 (2H, q, J=7.6 Hz), 7.52 (1H, d, J=8.4 Hz), 8.33 (1H, dd, J=2.5, 8.4 Hz), 8.90 (1H, d, J=2.5 Hz).

Step 2

N-Cyclopropylmethyl-2-ethyl-5-nitro-benzamide

2-Ethyl-5-nitrobenzoic acid (0.40 g), EDC.HCl (0.45 g), cyclopropylmethylamine (0.17 g) and hydroxybenzotriazole (0.04 g) were combined in dimethylformamide (10 ml) and stirred for 18 h. Solvent was removed at reduced pressure, the residue dissolved in dichloromethane and washed with 2N HCl and water. The organic phase was dried ($MgSO_4$) and solvent removed at reduced pressure to give the title compound (0.4 g). $^1$H NMR ($CDCl_3$) δ: 0.31 (2H, m), 0.59 (2H, m), 1.09 (1H, m), 1.28(3H, t, J=7.6Hz), 2.92 (2H, m), 3.33 (2H, m), 5.97 (1H, brs), 7.45 (1H, d, J=8.4 Hz), 8.20 (2H, m).

Step 3

5-Amino-N-cyclopropylmethyl-2-ethyl-benzamide

The title compound (0.32 g) was prepared from N-cyclopropylmethyl-2-ethyl-5-nitro-benzamide (0.40 g) according to the method of D21 step 2. $^1$H NMR ($CDCl_3$) δ: 0.26 (2H, m), 0.54 (2H, m), 1.03 (1H, m), 1.18 (3H, t, J=7.6 Hz), 2.67 (2H, q, J=7.6 Hz), 3.28 (2H, m), 5.85 (1H, brs), 6.69 (2H, m), 7.03 (1H, d, J=8.4 Hz).

The compound of D28 was used to prepare the compound of Example 37.

Description 29

6-Amino-2-methylaminobenzoxazole (D29)

Step 1

2-Methylamino-6-nitrobenzoxazole

2-Methylaminobenzoxazole (2.0 g, Hetzheim, Annemarie; Schlaak, G.; Kerstan, Christa., *Pharmazie,* (1987), 42, 80) was added in portions to conc. nitric acid (15 ml) at room temperature. Stirring was continued over 8 h. The reaction mixture was poured onto crushed ice/sodium hydrogen carbonate with vigorous stirring. The precipitated title compound (1.76 g) was collected by filtration and dried in vacuo at 40° C. m/z ($API^+$): 194 ($MH^+$).

Step 2

6-Amino-2-methylaminobenzoxazole

The title compound (1.31 g) was prepared from 2-methylamino-6-nitrobenzoxazole (1.50 g) according to the method of D21 step 2. $^1$H NMR ($CDCl_3$) δ: 3.07 (3H, d, J=3.4 Hz), 6.52 (1H, dd, J=2.1, 8.2 Hz), 6.65 (1H, d, J=2.1 Hz), 7.15 (1H, d, J=8.2 Hz).

The compound of D29 was used to prepare the compound of Example 73.

Description 30

(E)-3-(5-Amino-2-methoxy-phenyl)-N-methyl-acrylamide (D30).

Step 1

(E)-3-(5-Nitro-2-methoxy-phenyl)-N-methyl-acrylamide (E)-3-(2-Methoxy-5-nitro-phenyl)-acrylic acid (*Egypt. J. Pharm. Sci.,* (1996), 37, 71–84), (1.0 g) in dimethylformamide (5 ml) was treated with EDC.HCl (0.86 g), N-hydroxybenzotriazole (0.1 g) and methylamine (2M in tetrahydrofuran 3 ml) and stirred for 18 h. Solvent was removed at reduced pressure, the residue dissolved in dichloromethane, washed with 2N HCl, sodium hydrogen carbonate and brine. After drying ($MgSO_4$), solvent was removed at reduced pressure and the residue column chromatographed (silica gel, 5% methanol:dichloromethane) to give the title compound (0.75 g). $^1$H NMR δ: 2.71 (3H, d, J=4.7Hz), 4.01 (3H, s), 6.71 (1H, d, J=15.9 Hz), 7.30 (1H, d, J=9.2 Hz), 7.62 (1H, d, J=15.9 Hz), 8.09 (1H, m), 8.25 (1H, dd, J=2.8, 9.2 Hz), 8.36 (1H, d, J=2.8 Hz).

Step 2

(E)-3-(5-Amino-2-methoxy-phenyl)-N-methyl-acrylamide (E)-3-(5-Nitro-2-methoxy-phenyl)-N-methyl-acrylamide (0.75 g) and sodium sulphide (1.0 g) were combined in 1,4-dioxan/water (1:1, 20 ml) and warmed at 80° C. for 3 h. Solvent was removed at reduced pressure, the residue extracted with 10% methanol/dichloromethane and the extract filtered. The filtrate was evaporated to dryness and the residue column chromatographed (silica gel, 5% methanol:dichloromethane) to give the title compound (0.50 g). 1 H NMR δ: 2.68 (3H, d, J=0.4.8Hz), 3.71 (3H, s), 6.44 (1H, d, J=15.9 Hz), 6.60 (1H, dd, J=2.8 9.2 Hz), 6.73 (1H, d, J=2.8 Hz), 6.78 (1H, d, J=9.2 Hz), 7.57 (1H, d, J=15.9 Hz), 8.00 (1H, m).

The compound of D30 was used to prepare the compound of Example 38.

Description 31

3-Chloro-4-methanesulfonyloxybenzoic Acid (D31)

Sodium hydroxide (1.67 g) and 3-chloro-4-hydroxybenizoic acid (3.0 g) in water (30 ml) was stirred until dissolution was complete. Methanesulfonic anhydride (3.33 g) in dichloromethane (15 ml) was added with cooling (ice bath) and the mixture stirred for 48 h. The organic phase was separated and the aqueous phase acidified with colic. HCl. The precipitated colourless solid was separated by filtration, washed with water and recrystallised from methanol to give the title compound (1.85 g) as a colourless solid. m/z ($API^+$): 249, 251 ($MH^+$).

The compound of D31 was used for the preparation of Example 83.

Description 32

5-Amino-N-cyclopropylmethyl-2-methoxy-benzamide

Step 1

N-cyclopropylmethyl-2-methoxy-5-nitrobenzamide

A solution of 2-methoxy-5-nitrobenzoic acid (4.9 g) (*Rec. Trav. Chim. Pays-Bas,* 1936, 737) and cyclopropylmethylamine (1.75 g) in dimethylformamide was treated with N-hydroxybenzotriazole (0.2 g) and EDC.HCl (4.74 g). The mixture was stirred for 24 h. Saturated sodium hydrogen carbonate was added, the mixture stirred for 3 h and the precipitate collected as the title compound (6.95 g). m/z ($API^+$): 251 ($MH^+$).

Step 2

5-Amino-N-cyclopropylmethyl-2-methoxy-benzamide (2.57 g) was prepared from N-cyclopropylmethyl-2-methoxy-5-nitrobenzamide (3.6 g) according to the method of D21 step 2. m/z ($API^+$): 231 ($MH^+$). $^1$H NMR ($CDCl_3$) δ: 0.26 (2H, m), 0.51–0.55 (2H, m), 3.33 (1H, m), 3.55 (2H, brs), 3.90 (3H, s), 6.79 (2H, m), 7.56 (1H, dd, J=0.5, 2.8 Hz) 8.08 (1H, brs).

The compound of D32 was used for the preparation of Examples 32, 39 and 57.

4-Amino-8-chloro-2-methylquinoline is a known compound used for the preparation of example 45, *Indian J. Chem.,* Sect. B (1978), 16B(4), 329.

4-Amino-2,8-dimethylquinoline is a known compound used for the preparation of example 44, WO 92/22533.

4-Amino-2,6-dimethylquinoline is a known compound used for the preparation of example 42, *Dokl. Bolg. Akad. Nauk* (1977), 30(12), 1725–8.

4-Amino-2-N,N-dimethylaminoquinoline is a known compound used for the preparation of example 65 *Arch. Pharm.* (Weinheim, Ger.) (1986), 319(4), 347–54.

5-Amino-2-ethoxy-benzoic acid ethyl ester is a known compound used for the preparation of example 71 *Pralkr. Akad. Athenon* (1981), 55(A–B), 211–33.

6-Amino-2-methylbenzothiazole is a known compound used for the preparation of example 72 *Synthesis,* (1978), (5), 363.

4-Amino-2-methylquinoline is a commercially available compound used for the preparation of examples 6 and 54.

2-Methoxy-4-quinoline carboxylic acid is a known compound used for the preparation of examples 36 and 79 WO 92/12150.

EXAMPLE 1

1-(2-Methylbenzoxazol-6-yl)-3-(2-methylquinolin-4-yl)urea

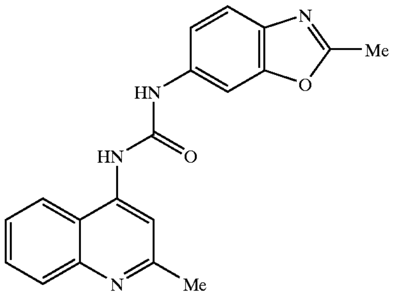

A slurry of 4-amino-2-methylquinoline (0.158 g) in dichloromethane (10 ml) was added to solution of carbonyl diimidazole (0.162 g) in dichloromethane (5 ml). The mixture was stirred for 2.5 h, solvent removed at reduced pressure and the residue dissolved in dimethylformamide (15 ml). 6-Amino-2-methylbenzoxazole (0.148 g) (*Res. Inst. Drugs, Modra, Slovakia. Collect. Czech. Chem. Commun.* (1996), 61, 371–380) was added and the mixture warmed to 100° C. for 1 h. Solvent was removed at reduced pressure and triturated with diethyl ether and methanol to give the title compound (0.035 g) as a colourless solid. 1 H NMR δ: 2.59 (3H, s), 2.60 (3H, s), 7.24 (1H, dd, J=1.9, 8.5 Hz), 7.58–7.63 (2H, m), 7.73 (1H, t, J=7.2 Hz),7.89 (1H, d, J=7.7 Hz), 8.06 (1H, d, J=1.8 Hz), 8.13–8.15 (2H, m), 9.22 (1H, brs), 9.55 (1H, brs). m/z ($API^+$): 333 ($MH^+$).

EXAMPLE 2

1-(4-Dimethylaminophenyl)-3-(2-methylquinolin-4-yl)urea

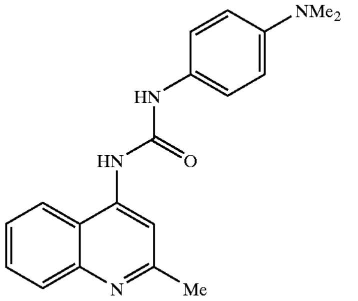

4-N,N-Dimethylaminophenyl isocyanate (0.162 g) was added to a stirred solution of 4-amino-2-methylquinoline (0.158 g) in dichloromethane (20 ml) containing 4-N,N-dimethylaminopyridine (2 mg). The mixture was stirred for 16 h under argon, diluted with diethyl ether (20 ml) and the precipitated solid collected by filtration and washed with diethyl ether to give the title compound (0.146 g) as a colourless solid. $^1$H NMR δ: 2.61 (3H, s), 2.86 (6H, s), 6.74 (2H, d, J=9.0 Hz), 7.33 (2H, d, J=9.0 Hz), 7.58 (1H, t, J=7.0 Hz) 7.71 (1H, t, J=7.6 Hz), 7.87 (1H, d, J=8.3 Hz), 8.13 (1H, d, J=8.5 Hz), 8.15 (1H, s) 8.98 (1H, s), 9.04 (1H, s).

EXAMPLE 3

1-(2-Methylbenzoxazol-6-yl)-3-(2-chloroquinolin-4-yl)urea

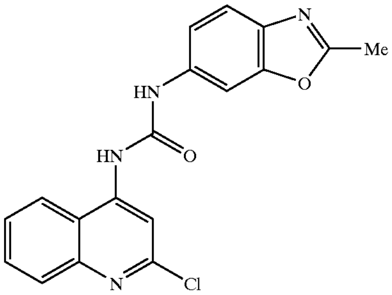

2-Chloro-4-chlorocarbonylquinoline (0.5 g), prepared by standard methods from 2-chloroquinoline-4-carboxylic acid, was added to sodium azide in aqueous dioxan (2.1 ml 1:3) at 0° C. Acetone was then added and the mixture stirred for 16 h. Water (10 ml) was added, the precipitated solid collected by filtration and air dried to give 2-chloroquinoline-4-carbonyl azide (0.455 g). The azide (0.232 g) in toluene (10 ml) was warmed from room temperature to 75° C. and then heating continued for 1 h. After cooling to room temperature 6-amino-2-methylbenzoxazole (0.148 g) in dichloromethane (15 ml) containing 4-N,N-dimethylaminopyridine (20 mg) was added and the mixture stirred for 16 h. The precipitated solid was separated by filtration to give a solid (0.25 g). Column chromatography (silica gel, dichloromethane/methanol/ammonia mixtures) gave the title compound (0.072 g). $^1$H NMR δ: 5 2.60 (3H, s), 7.25 (1H, d, J=8.5 Hz), 7.61 (1H, d, J=8.5 Hz), 7.73 (1H, t, J=7.0 Hz), 7.84 (1H, t, J=6.7 Hz), 7.91 (1H, d, J=8.0 Hz), 8.05 (1H, s), 8.20 (1H, d, J=8.25 Hz), 8.28 (1H, s), 9.49 (1H, s), 9.61 (1H, s). m/z ($API^+$): 353, 355($MH^+$).

EXAMPLE 4

1-(4-N,N-Dimethylaminophenyl)-3-(2-chloroquinolin-4-yl)urea

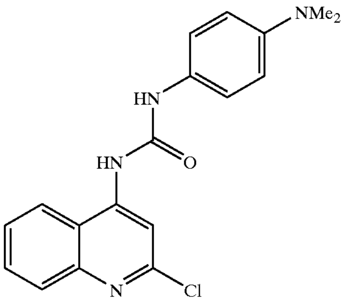

From 2-chloroquinoline-4-carbonyl azide (1.5 g), (see example 3) and 4-N,N-dimethylphenylenediamine (0.88 g) the title compound was prepared according to the method of example 3. $^1$H NMR δ: 2.87 (6H, s), 6.75 (2H, d, J=9.0 Hz), 7.33 (2H, d, J=9.0 Hz), 7.67–7.99 (4H, m), 8.17–8.31 (3H, m), 9.05 (1H, s), 9.34 (1H, s). m/z ($API^+$): 341, 343 ($MH^+$).

EXAMPLE 5

1-(3-Butyryl-4-methoxyphenyl)-3-(5,8-difluoroquinolin-4-yl)urea

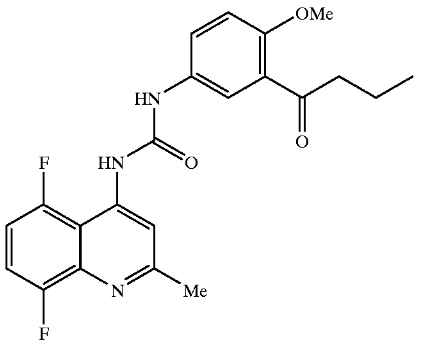

To a suspension of 3-butyryl-4-methoxybenzoic acid (0.111 g) in toluene (4 ml), triethylamine (0.21 ml) and diphenylphosphoryl azide (0.11 ml) were added. The mixture was stirred for 16 h, quinoline D1 (0.097 g) added and mixture boiled for 4 h. Solvent was removed at reduced pressure and the residue column chromatographed (silica gel, 0–10% methanol containing 1% ammonia:dichloromethane) to give the title compound (0.02 g). $^1$H NMR δ: 0.74 (3H, m), 1.42 (2H, m), 2.45 (3H, s), 2.74 (2H, t, J=7.2 Hz), 3.70 (3H, s), 6.99 (1H, d, J=8.8 Hz), 7.17 (1H, m), 7.33–7.53(3H, m), 8.15 (1H, s), 8.67 (1H, d, J=15 Hz), 9.78 (1H, s). m/z (API$^+$): 414 (MH$^+$).

EXAMPLES 6–20, 64, 83

Were prepared by standard methods illustrated by Example 5 using the appropriate aminoquinoline and carboxylic acid.

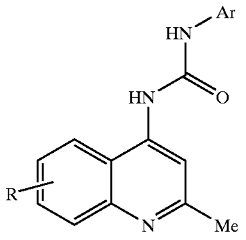

| e.g. | Quinoline used | R | Ar | yield | MS (API+) |
|---|---|---|---|---|---|
| 6 | — | H | 3-Br, 4-SMe$C_6H_3$ | 22% | MH+ 402, 404 |
| 7 | D2 | 6,8-diF | 4-MeS, 3-COMe$C_6H_3$ | 2.8% | MH+ 402 |
| 8 | D3 | 8-F | 4-MeO, 3-CN$C_6H_3$ | 84% | MH+ 351 |
| 9 | D1 | 5,8-diF | 4-MeO, 3-COMe$C_6H_3$ | 52% | MH+ 386 |
| 10 | D1 | 5,8-diF | 4-Cl, 3-COMe$C_6H_3$ | 45% | MH+ 390 |
| 11 | D3 | 8-F | 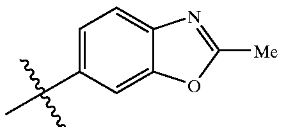 | 56% | MH+ 351 |
| 12 | D2 | 6,8-diF | 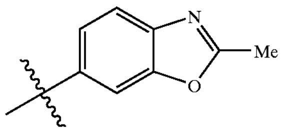 | 5% | MH+ 369 |
| 13 | D3 | 8-F | 4-MeO, 3-COPr$C_6H_3$ | 38% | MH+ 396 |
| 14 | D2 | 6,8-diF | 3-Cl, 4-OEt$C_6H_3$ | 22% | MH+ 393 |
| 15 | D2 | 6,8-diF | 3-MeO, 4-Me$C_6H_3$ | 2% | MH+ 358 |
| 16 | D1 | 5,8-diF | 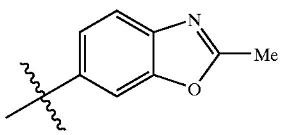 | 5% | MH+ 369 |

-continued
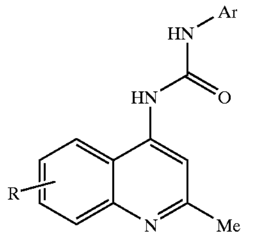
| e.g. | Quinoline used | R | Ar | yield | MS (API+) |
|---|---|---|---|---|---|
| 17 | D4 | 5,6-diF | 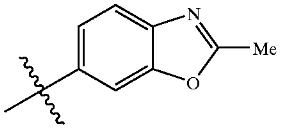 | 7% | MH+ 369 |
| 18 | D5 | 5,7-diF | 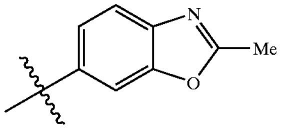 | 10% | MH+ 369 |
| 19 | D6 | 6-Cl | 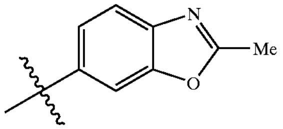 | 18% | MH+ 366, 368 |
| 20 | D7 | 7,8-diF | 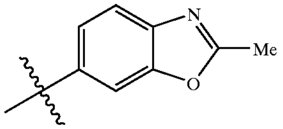 | 3% | MH+ 369 |
| 64 | D1 | 5,8-diF | 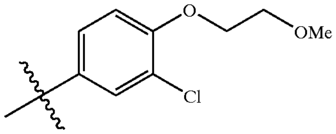 | 32% | MH+ 422 |
| 83 | D1 | 5,8-diF | 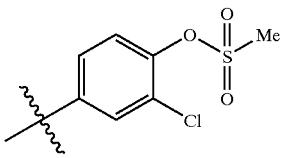 | 37% | MH+ 442 |
$^1$H NMR spectra were consistent with the structures in the table.

Examples 21–38, 79 were prepared by standard methods illustrated by Example 5 using appropriate quinoline carboxylic acid and aniline.
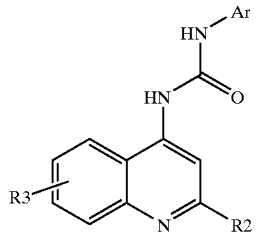
| e.g. | Quinoline | $R^2$ | $R^3$ | Ar | yield | MS (API+) |
|---|---|---|---|---|---|---|
| 21 | D19 | Me | 8-Et | 4-$NMe_2C_6H_4$ | 14% | MH+ 349 |
| 22 | D17 | Me | 8-F | 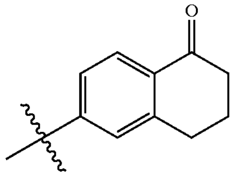 | 83% | MH+ 364 |
| 23 | D17 | Me | 8-F | 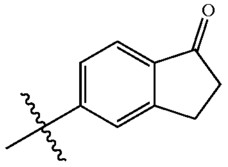 | 51% | MH+ 350 |
| 24 | D17 | Me | 8-F | 4-$CO_2Et$—$C_6H_4$ | 32% | MH+ 368 |
| 25 | D17 | Me | 8-F | 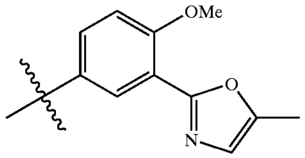 | 25% | MH+ 407 |
| 26 | D13 | F | H | 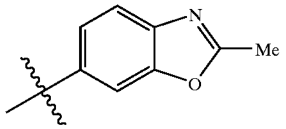 | 30% | MH+ 337 |
| 27 | D13 | F | H | 4-$NMe_2C_6H_4$ | 8% | MH+ 324 |
| 28 | D12 | SMe | H | 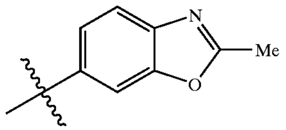 | 80% | MH+ 365 |
| 29 | D15 | Cl | 8-F | 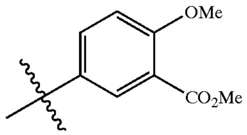 | 46% | MH+ 404 |
| 30 | D15 | Cl | 8-F | 4-$NMe_2C_6H_4$ | 44% | MH+ 359 |
| 31 | D15 | Cl | 8-F | 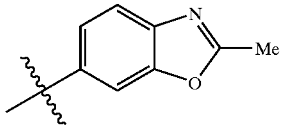 | 61% | MH+ 371 |

-continued
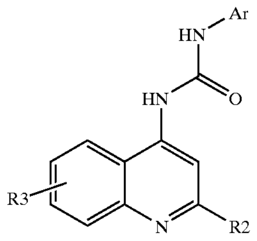
| e.g. | Quinoline | $R^2$ | $R^3$ | Ar | yield | MS (API+) |
|---|---|---|---|---|---|---|
| 32 | D16 | OMe | 8-F | 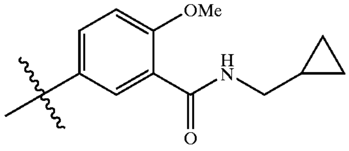 | 55% | MH+ 439 |
| 33 | D16 | OMe | 8-F | 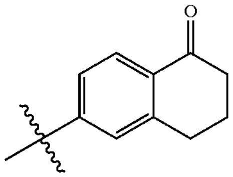 | 93% | MH+ 380 |
| 34 | D16 | OMe | 8-F | 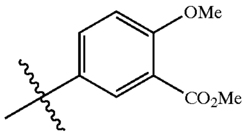 | 54% | MH+ 400 |
| 35 | D16 | OMe | 8-F | $4\text{-}NMe_2C_6H_4$ | 28% | MH+ 355 |
| 36 | known | OMe | H | 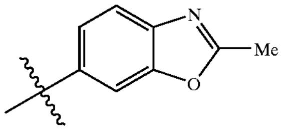 | 66% | MH+ 349 |
| 37 | D17 | Me | 8-F | 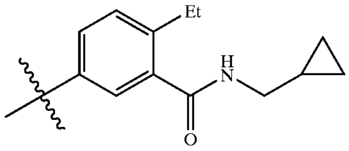 | 95% | MH+ 421 |
| 38 | D17 | Me | 8-F | 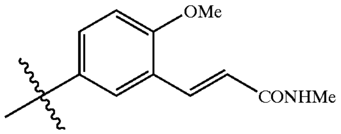 | 43% | MH+ 409 |
| 79 | known | OMe | H | 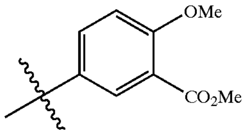 | 40% | MH+ 382 |
$^1$H NMR spectra were consistent with the structures in the table

EXAMPLE 39

N-Cyclopropylmethyl-5-[3-(8-fluoro-2-methyl-quinolin-4-yl)-ureido]-2-methoxy-benzamide Hydrochloride

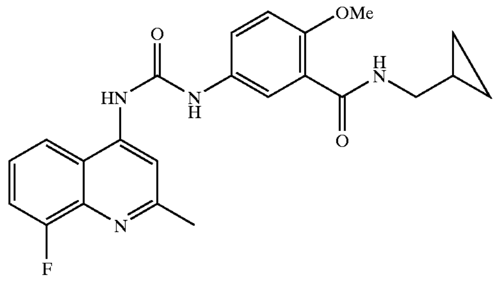

The title compound (0.265 g) as the free base was prepared from acid D17 (0.205 g) and 5-amino-N-cyclopropylmethyl-2-methoxy-benzamide (0.22 g) according to the method of example 5. The hydrochloride salt (0.095 g) was prepared from the free base (0.10 g) by dissolving in methanol and treating with ethereal HCl. m/z ($API^-$); 423 ($MH^+$). $^1$H NMR ($CDCl_3$) δ: 0.24–0.26 (2H, m), 0.41–0.46 (2H, m), 0.99–1.10 (1 h, m), 2.82 (3H, s) 3.19 (1H, t, J=6.5 Hz), 3.89 (3H, s), 7.16 (1H, d, J=9.1Hz), 7.67 (1H, dd, J=2.8, 8.9 Hz), 7.74 (1H, m), 7.84–7.92 (1H, m), 7.95 (1H, d), 8.25 (1H, t), 8.60 (1H, s), 8.95 (1H, brd), 11.04 (1H, brs), 11.17 (1H, brs).

EXAMPLES 40–49, 65, 82

Were prepared by standard methods illustrated by either Example 2 or below for Example 40 using the appropriate aminoquinoline and isocyanate.

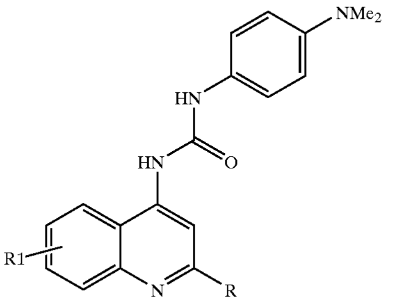

The amine D1 (0.097 g) was added to sodium hydride (60% suspension in oil, 0.024 g) in dimethylformamide (5 ml). After 1 h gas evolution had ceased and 4-dimethylaminophenylisocyanate (0.081 g) added and the mixture stirred for 2 h. Water was added to the mixture and the precipitated product collected by filtration and washed with water and diethyl ether to give the desired product (0.14 g).

| e.g. | Quinoline used | method | R | $R^1$ | yield | MS (API+) |
|---|---|---|---|---|---|---|
| 40 | D1 | 40 | Me | 5,8-diF | 80% | MH + 357 |
| 41 | D7 | 40 | Me | 7,8-diF | 73% | MH + 357 |
| 42 | known | 2 | Me | 6-Me | 30% | MH + 335 |
| 43 | D4 | 40 | Me | 6,7-diF | 33% | MH + 357 |
| 44 | known | 2 | Me | 8-Me | 66% | MH + 335 |
| 45 | known | 2 | Me | 8-Cl | 53% | MH + 355 |
| 46 | D11 | 40 | Me | 8-Cl-7-Me | 23% | MH + 369, 371 |
| 47 | D8 | 2 | Me | 6-F | 24% | MH + 339 |
| 48 | D11 | 2 | Me | 8-CH:CH2 | 7% | MH + 347 |
| 49 | D4 | 40 | Me | 5,6-diF | 38% | MH + 357 |
| 65 | known | 2 | $NMe_2$ | H | 34% | MH + 350 |
| 82 | D9 | 2 | Me | 8-Br | 32% | MH + 399, 401 |

$^1$H NMR spectra were consistent with the structures in the table

EXAMPLE 50

1-(4-Acetyl-phenyl)-3-(8-fluoro-2-methyl-quinolin-4-yl)-urea

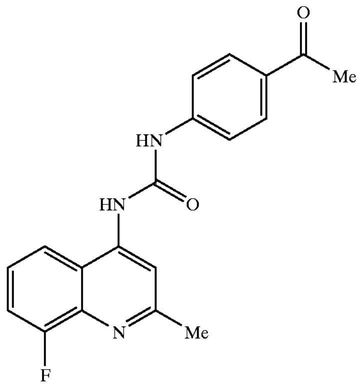

The title compound (0.60 g) was prepared from quinoline D3 (0.40 g) and 4-acetylphenyl isocyanate (0.367 g) according to the method of Example 2. m/z ($API^+$): 338 ($MH^+$). $^1$H NMR δ: 2.54 (3H, s), 2.64 (3H, s), 7.54–7.61 (1H, m), 7.66 (1H, d, J=5.5Hz), 7.96 (1H, m), 8.22 (1H, s), 9.30 (1H, s), 9.68 (1H, s).

EXAMPLE 51

1-(6,8-Difluoro-2-methyl-quinolin-4-yl)-3-(4dimethylaminophenyl)-urea

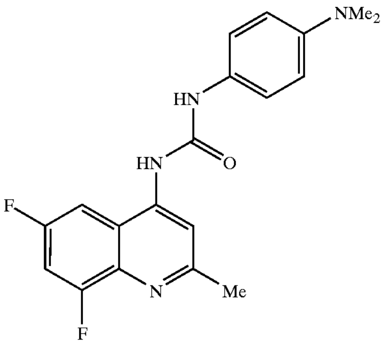

The title compound (0.08 g) was prepared from quinoline D2 (0.19 g) and 4-dimethylaminophenyl isocyanate (0.16 g) according to the method of Example 40. m/z ($API^+$): 357 ($MH^+$). $^1H$ NMR δ: 2.60 (3H, s), 2.82 (6H, s), 6.74 (2H, d, J=9.0Hz), 7.33 (2H, d, J=9.0 Hz), 7.65–7.80 (2H, m), 8.25 (1H, s), 8.89 (1H, s), 8.99 (1 H, s).

EXAMPLES 52–55, 80

We prepared by standard methods illustrated by Example 1 from the appropriate aminoquinoline and aniline.

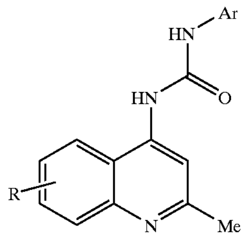

| e.g. | Quinoline used | R | Ar | yield | MS (API+) |
|---|---|---|---|---|---|
| 52 | D3 | 8-F | 3-MeO, 5-$CO_2MeC_6H_3$ | 7% | MH+ 384 |
| 53 | D2 | 6,8-diF | 4-MeO, 3-$MeOCH_2C_6H_3$ | 2% | MH+ 388 |
| 54 | known | H | 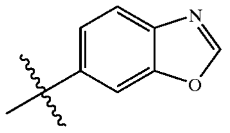 | 20% | MH+ 319 |
| 55 | D2 | 6,8-diF | 4-MeO, 3-$MeC_6H_3$ | 26% | MH+ 358 |
| 80 | D2 | 6,8-diF | 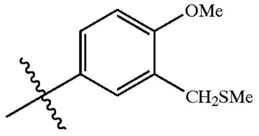 | 6% | MH+ 404 |

$^1H$ NMR spectra were consistent with the structures in the table

EXAMPLE 56

1-(5,8-Difluoro-2-methyl-quinolin-4-yl)-3-(5-oxo-5,6,7,8-tetrahydro-naphthalen-2-yl)-urea

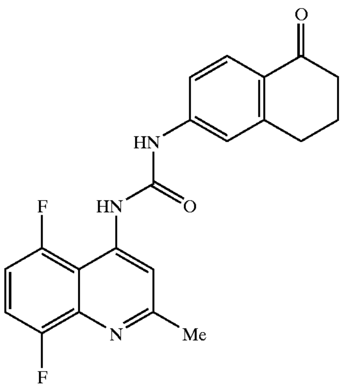

The title compound (0.23 g) was prepared according to the method of Example 1 from quinoline D1 (0.42 g) and 6-amino-1,2,3,4-tetrahydronaphthalen-1-one (0.35 g). m/z ($API^+$): 382 ($MH^+$). $^1H$ NMR δ: 1.09–2.07 (2H, m), 2.55 (2H, m), 2.64 (3H, s), 2.91 (2H, m) 7.32–7.42 (2H, m), 7.52–7.58 (2H, m), 7.85 (1H, d, J=5.3 Hz), 8.29 (1H, s), 9.00 (1H, brs), 10.26 (1H, brs).

EXAMPLE 57

N-Cyclopropylmethyl-5-[3-(5,8-difluoro-2-methyl-quinolin-4yl)-ureido]-2-methoxy-benzamide

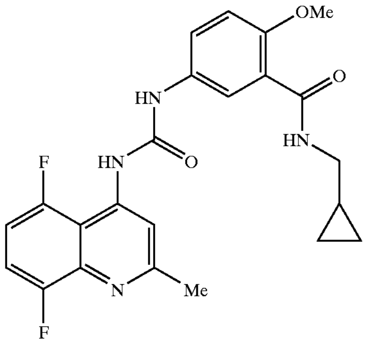

The title compound (0.11 g) was prepared according to the method of Example 1 from quinoline D1 (0.22 g) and 5-amino-N-cyclopropylmethyl-2-methoxy-benzamide (0.23 g). m/z (API$^{31}$ ): 441 ($MH^+$). $^1$H NMR δ: 0.25 (2H, m)<0.44 (2H, m), 1.05 (1H, m), 2.62 (3H, s), 3.19 (2H, t, J=3.8 Hz), 3.89 (3H, s), 7.13 (1H, d, J=5.8 Hz), 7.31–7.35 (1H, m), 7.52–7.56 (1H, m), 7.69 (1H, dd, J=2, 5.5 Hz), 7.88 (1H, d, J=2 Hz), 8.26 (1H, t, J=3.5 Hz), 8.84 (1H, brd), 9.95 (1H, brs)

EXAMPLES 58–63

Were prepared by a standard method illustrated below for Example 58 from the appropriate ketone.

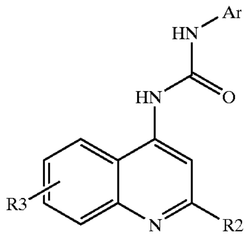

EXAMPLE 58

1-(8-Fluoro-2-methoxy-quinolin-4-yl)-3-(5-hydroxy-5,6,7,8-tetrahydro-naphthalen-2-yl)-urea The quinoline of Example 33 (0.091 g) was suspended in methanol (10 ml). Sodium borohydride (0.064 g) was added and the mixture stirred for 3 h. Dichloromethane (5 ml) was added to assist solubilisation of material and stirring continued for a further 2 h. Solvent was removed at reduced pressure, the residue partitioned between dichloromethane/water, the organic phase dried ($MgSO_4$), solvent removed at reduced pressure and the residue column chromatographed (silica gel, 0–10% [9:1 methanol:ammonia] in dichloromethane) to give the title compound (0.009 g). $^1$H NMR δ: 1.69 (2H, m), 2.67 (2H, m), 3.98 (3H, s), 4.53 (1H, m), 5.02 (1H, d, J=5.7 Hz), 7.23–7.25 (2H, m), 7.34 (1H, m), 7.44–7.59 (2H, m), 7.80 (1H, s), 7.90 (1H, d, J=8.1 Hz), 9.17 (1H, brs), 9.24 (1H, brs).

| e.g. | Ketone | R2 | R3 | Ar | yield | MS (API) |
|---|---|---|---|---|---|---|
| 58 | e.g. 33 | OMe | 8-F | 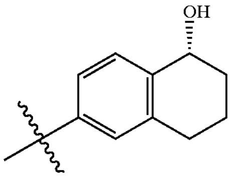 | 10% | MH+ 382 |
| 59 | e.g. 22 | Me | 8-F | 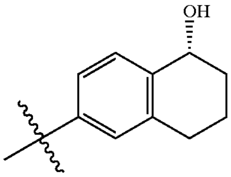 | 60% | MH+ 366 |
| 60 | e.g. 23 | Me | 8-F | 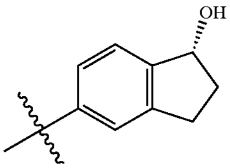 | 79% | MH+ 352 |
| 61 | e.g. 13 | Me | 8-F | 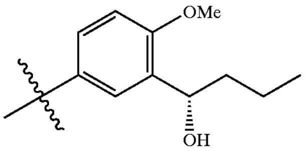 | 74% | MH+ 398 |
| 62 | e.g. 56 | Me | 5,8-diF | 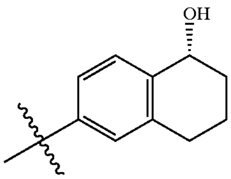 | 9% | MH+ 384 |

-continued

| e.g. | Ketone | R2 | R3 | Ar | yield | MS (API) |
|---|---|---|---|---|---|---|
| 63 | e.g. 50 | Me | 8-F | 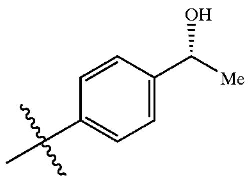 | 76% | MH+ 340 |

$^1$H NMR spectra were consistent with the structures in the table

EXAMPLES 66–74

Were prepared by a standard method illustrated below for Example 66.

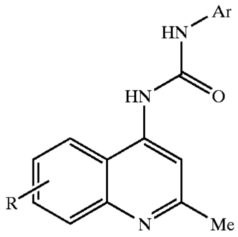

A mixture of the trichlorocetamide D24 (0.17 g) DBU (0.076 g) and 6-aminoindole (*J. Amer. Chem. Soc.* 1954, 76, 5149) (0.066 g) were combined in DMSO (5 ml) and warmed to 80° C. for 1 h and at 110° C. for 4 h. After cooling the reaction mixture was diluted with ethyl acetate, washed with water (×3), dried ($Na_2SO_4$) and solvent removed at reduced pressure. The residue was column chromatographed (silica gel, dichloromethane-4% methanol/dichloromethane) to give after combining appropriate fractions and converting to the hydrochloride salt the title compound (0.01 g). (Method A). m/z ($API^+$): 353 ($MH^+$). $^1$H NMR δ: 2.79 (3H, s), 6.39 (1H, m), 7.03 (1H, dd, J=1.8, 8.5 Hz), 7.30 (1H, m), 7.49 (1H, d, J=8.5 Hz), 7.86 (1H, s), 8.07 (1H, t), 8.58 (2H, m), 10.41 (2 H, m), 11.07 (1H, s). Alternatively instead of using DMSO as solvent DMSO containing pyridine (5% by volume) can be used (Method B)

| e.g. | Acetamide | Method | R | Ar | yield | MS (API+) |
|---|---|---|---|---|---|---|
| 66 | D24 | A | 6,8-diF | 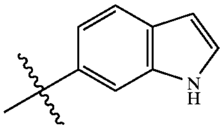 | 5 | MH+ 353 |
| 67 | D20 | B | 8-F | 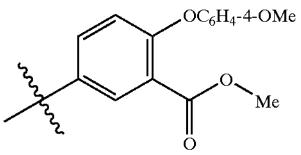 | 7 | MH+ 476 |
| 68 | D20 | B | 8-F | 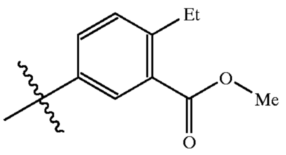 | 4 | MH+ 382 |
| 69 | D22 | B | 6,8-diF | 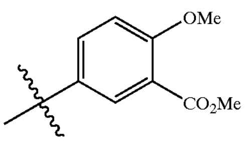 | 32 | MH+ 402 |

-continued

| e.g. | Acetamide | Method | R | Ar | yield | MS (API+) |
|---|---|---|---|---|---|---|
| 70 | D20 | B | 8-F | 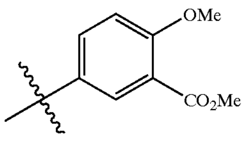 | 31 | MH+ 384 |
| 71 | D20 | B | 8-F | 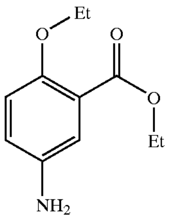 | 29 | MH+ 412 |
| 72 | D24 | A | 6,8-diF | 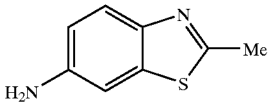 | 4 | MH+ 385 |
| 73 | D25 | A | 8-F | 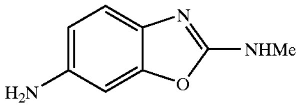 | 6 | MH+ 366 |
| 74 | D23 | B | 5,8-diF | 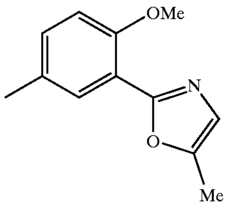 | 12 | MH+ 425 |

$^1$H NMR spectra were consistent with the structures in the table

EXAMPLE 75

1-(3-Chloro-4-methoxy-phenyl)-3-(5,8-difluoro-2-methyl-quinolin-4-yl)-urea

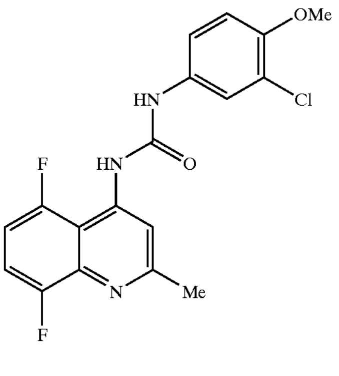

Title compound (0.005 g) was prepared according to the method of Example 66 from acetamide D23 (0.118 g) and 3-chloro-4-methoxyaniline (0.039 g) but using pyridine as solvent. m/z ($API^+$): 378 ($MH^+$). $^1$H NMR δ: 2.62 (3H, s), 3.83 (1H, s), 7.13 (1H, d, J=9.0 Hz ), 7.28–7.40 (2H, m), 7.50–7.60 (1H, m), 7.74 (1H, d, J=2.6 Hz), 8.29 (1H, s), 8.86 (1H, d), 9.93 (1H, s).

EXAMPLES 76–78, 81

Were prepared by a standard method illustrated below for Example 76, by treating the appropriate ester with the corresponding primary amine

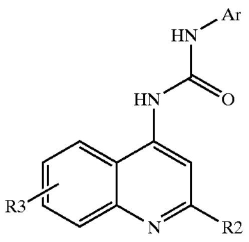

A mixture the compound of example 29 (0.02 g) and cyclopropylmethylamine (2 ml) were stood at room temperature for 72 h. Solvent was removed at reduced pressure and the residue triturated with ethyl acetate/diethyl ether to give the title compound. m/z ($API^-$): 445 ($MH^+$). $^1$H NMR δ: 0.26 (2H, m), 0.41–0.46 (2H, m), 1.05 (1H, m), 3.19 (2H, t, J=6.2 Hz), 3.89 (3H, s), 7.15 (1H, d, J=9.0 Hz), 7.65–7.73 (3H, m), 7.87 (1H, d, J=2.7 Hz), 8.09 (1H, m), 8.29 (1H, m), 8.35 (1H, s), 9.57 (1H, s).

| e.g. | ester e.g. | R2 | R3 | Ar | yield | MS (API+) |
|---|---|---|---|---|---|---|
| 76 | 29 | Cl | 8-F | 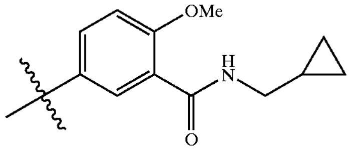 | 59% | MH+ 443, 445 |
| 77 | 71 | Me | 8-F | 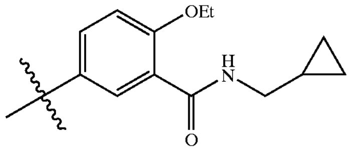 | 30% | MH+ 437 |
| 78 | 69 | Me | 6,8-diF | 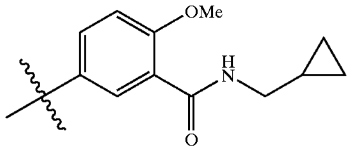 | 55% | MH+ 441 |
| 81 | 79 | OMe | H | 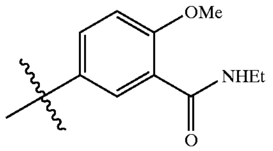 | 48% | MH+ 395 |

$^1$H NMR spectra were consistent with the structures in the table

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (MEM medium with Earl's salts) containing 2 mM L-Glutamine, 0.4 mg/mL G418 Sulfate from GIBCO BRL and 10% heat inactivated fetal calf serum from Gibco BRL. The cells were seeded at 20,000 cells/100 $\mu$l/well into 96-well black clear bottom sterile plates from Costar which had been pre-coated with 10 $\mu$g/well of poly-L-lysine from SIGMA. The seeded plates were incubated overnight at 37° C. in 5% $CO_2$. Agonists were prepared as 1 mM stocks in water:DMSO (1:1). $ECo_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11×half log unit dilutions in Tyrode's buffer containing 10% DMSO and probenecid. On the day of assay 50 $\mu$l of cell medium containing probenecid (Sigma) and Fluo3AM (Texas Fluorescence Laboratories) was added (Quadra, Tomtec) to each well to give final concentrations of 2.5 mM and 4 $\mu$M, respectively. The 96-well plates were incubated for 90 min at 37° C. in 5% $CO_2$. The loading solution containing dye was then aspirated and cells were washed with 4×150 $\mu$l Tyrode's buffer containing probenecid and 0.1% gelatin (Denley Cell Wash). The volume of buffer left in each well was 125 $\mu$l. Antagonist or buffer (25 $\mu$l) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, 1995, *TiPS,* 16, 413417) to generate a concentration effect value. Antagonist $K_b$ values were calculated using the equation:

$$K_b IC_{50}/(1+([3/EC_{50}])$$

where $EC_{50}$ was the potency of human orexin-A determined in the assay (in nM terms) and $IC_{50}$ is expressed in molar terms.

As an illustration of the activity of the compounds of formula (I), the compounds of Examples 1 and 2 each had a pkb>6.0 in this assay.

What is claimed is:

1. A compound of formula (I):

(I)

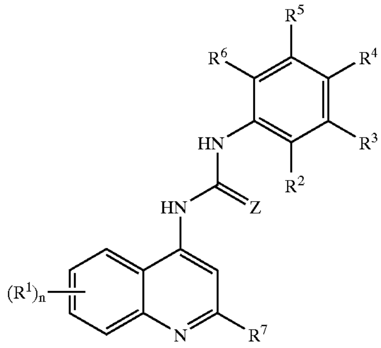

in which:

Z represents oxygen or sulfur;

$R^1$ represents $(C_{1-6})$alkyl, $(C_{2-6})$alkenyl or $(C_{1-6})$alkoxy, any of which may be optionally substituted; halogen, $R^8$CO— or $NR^9R^{10}$CO—;

$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkylthio, any of which may be optionally substituted; hydrogen, halogen, nitro, cyano, aryloxy, aryl$(C_{1-6})$alkyloxy, aryl$(C_{1-6})$alkyl, $R^8$CO—, $R^8SO_2$NH—, $R^8SO_2$O—, $R^8CON(R^{11})$—, $NR^9R^{10}$—, $NR^9R^{10}$CO—, —$COOR^9$, $R^{11}C(=NOR^8)$, heterocyclyl or heterocyclyl$(C_{1-6})$alkyl;

or an adjacent pair of $R^2$, $R^3$, $R^4$, $R^5$ and $R^6$ together with the carbon atoms to which they are attached form an optionally substituted carbocyclic or heterocyclic ring;

$R^7$ is $(C_{1-6})$alkyl, $(C_{2-6})$alkenyl, $(C_{1-6})$alkoxy or $(C_{1-6})$alkylthio, any of which may be optionally substituted; halogen, hydroxy, nitro, cyano, $NR^9R^{10}$—, $NR^9R^{10}$CO—, $N_3$, —$OCOR^9$ or $R^8CON(R^{11})$—;

$R^8$ is $(C_{1-6})$alkyl, $(C_{2-6})$alkenyl, heterocyclyl, heterocyclyl$(C_{1-6})$alkyl, heterocyclyl$(C_{2-6})$alkenyl, aryl, aryl$(C_{1-6})$alkyl or aryl$(C_{2-6})$alkenyl, any of which maybe optionally substituted;

$R^9$ and $R^{10}$ independently represent hydrogen, $(C_{1-6})$alkyl, $(C_{2-6})$alkenyl, heterocyclyl, heterocyclyl$(C_{1-6})$alkyl, aryl or aryl$(C_{1-6})$alkyl, any of which maybe optionally substituted;

$R^{11}$ is hydrogen or $(C_{1-6})$alkyl; and n is 0, 1, 2, or 3;

or a pharmaceutically acceptable salt thereof, provided that the compound is not:

a) N-(2-methyl-4-quinolinyl)-N'-[3-(trifluoromethyl)phenyl]urea;
b) N-(4-methoxyphenyl)-N'-(2-methyl-4-quinolinyl)urea;
c) N-[3-(dimethylamino)phenyl]-N'-(2-methyl-4-quinolinyl)urea;
d) N-(3-methoxyphenyl)-N'-(2-methyl-4-quinolinyl)urea;
e) ethyl 3-[[[(2-methyl-4-quinolinyl)amino]carbonyl]amino]benzoate;
f) N-[3-hydroxyphenyl]-N'-(2-methyl-4-quinolinyl)urea;
g) N-[2,3-dichlorophenyl]-N'-(2-methyl-4-quinolinyl)urea;
h) N-benzo[b]thien-5-yl-N'-(2-methyl-4-quinolinyl)urea;
i) N-(1-methyl-1H-indol-5-yl)-N'-(2-methyl-4-quinolinyl)urea;
j) N-(2-methyl-4-quinolinyl)-N'-(5,6,7,8-tetrahydro-1-naphthalenyl)urea;
k) N-(2-methyl-4-quinolinyl)-N'-(3,4,5-trimethoxyphenyl)urea;
l) N-(2-methylphenyl)-N'-(2-methyl-4-quinolinyl)urea;
m) N-(4-methylphenyl)-N'-(2-methyl-4-quinolinyl)urea;
n) N-(3,5-dimethylphenyl)-N'-(2-methyl-4-quinolinyl)urea;
o) N-(4-chlorophenyl)-N'-(2-methyl-4-quinolinyl)urea;
p) N-(2-methyl-4-quinolinyl)-N'-[3-(trifluoromethyl)phenyl)urea;
q) N-(2-methoxyphenyl)-N'-(2-methyl-4-quiolinyl)urea;
r) N-(2-methyl-4-quinolinyl)N'-phenylurea;
s) N-(3,4-dimethylphenyl)-N'-(2-methyl-4-quinolinyl)urea;
t) N4-methyl-2-nitrophenyl)-N'-(2-methyl-4-quinolinyl)urea;
u) N-(3-chloro-4-methylphenyl)-N'-(2-methyl-4-quinolinyl)urea;
v) N-(5-chloro-2-methoxyphenyl)-N'-(2-methyl-4-quinolinyl)urea;
w) 1-(6amino-2-methyl-4-quinolinyl)-3-(o-nitrophenyl)urea; or
x) N-(1,2-dihydro-6-methyl-2-oxo-4-quinolinyl)-N'-phenylthiourea.

2. A compound according to claim 1 in which Z represents oxygen.

3. A compound according to claim 1 in which n is 1 or 2.

4. A compound according to claim 1 in which $R^2$ to $R^6$ independently represent hydrogen, $R^8$CO—, $NR^9R^{10}$ CO—, halogen, $(C_{1-6})$alkoxy, $(C_{1-6})$alkylthio, or $NR^9R^{10}$, and at least one of $R^2$ to $R^6$ is other than hydrogen; or an adjacent pair of $R^2$ to $R^6$ together with the carbon atoms to which they are attached form an optionally substituted 5- to 7-membered carbocyclic or heterocyclic ring.

5. A compound according to claim 1 in which $R^2$, $R^5$ and $R^6$ represent hydrogen.

6. A compound according to claim 1 in which $R^2$, $R^4$ and $R^6$ represent hydrogen.

7. A process for the preparation of a compound of formula (I) according to claim 1, or a salt thereof which comprises coupling a compound of formula (II):

(II)

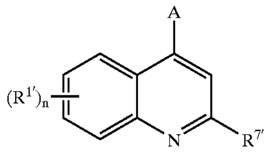

with a compound of formula (III):

(III)

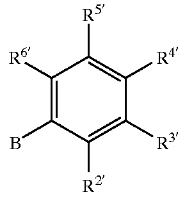

where A and B are appropriate functional groups to form the —NHCONH— or —NHCSNH— moiety when coupled; n is as defined in formula (I); and $R^{1'}$ to $R^{7'}$ are $R^1$ to $R^7$ as defined in formula (I) or groups convertible thereto; and thereafter optionally and as necessary and in any appropriate order, converting any $R^{1'}$ to $R^{7'}$ when other than $R^1$ to $R^7$ respectively to $R^1$ to $R^7$, and/or forming a pharmaceutically acceptable salt thereof.

8. A compound library comprising at least 2 compounds of formula (I) as defined in claim 1, or pharmaceutically acceptable salts thereof.

9. A pharmaceutical composition comprising a compound of formula (I) as defined in claim 1, or a pharmaceutically acceptable salt thereof, and a pharmaceutically acceptable carrier.

10. A method of treating or preventing a disease or disorder where an antagonist of a human orexin receptor is required, which comprises administering to a subject in need thereof an effective amount of a compound of formula (I) as defined in claim 1, or a pharmaceutically acceptable salt thereof, provided that the compound is not N-(2-methyl-4-quinolinyl)-N'-phenylurea.

11. A compound according to claim 1:

1-(2-methylbenzoxazol-6-yl)-3-(2-methylquinolin-4-yl) urea, 1-(4-dimethylaminophenyl)-3-(2-methylquinolin-4-yl)urea, 1-(2-methylbenzoxazol-6-yl)-3-(2-chloroquinolin-4-yl) urea, 1-(4-N,N-dimethylaminophenyl)-3-(2-chloroquinolin-4-yl) urea, 1-(3-butyryl-4-methoxyphenyl)-3-(5,8-difluoroquinolin-4-yl)urea, N-cyclopropylmethyl-5-[3-(8-fluoro-2-methyl-quinolin-4-yl)-ureido]-2-methoxy-benzamide hydrochloride, 1-(4-acetyl-phenyl)-3-(8-fluoro-2-methyl-quinolin-4-yl)-urea, 1-(6,8-difluoro-2-methyl-quinolin-4-yl)-3-(4-dimethylamino-phenyl)-urea, 1-(5,8-difluoro-2-methyl-quinolin-4-yl)-3-(5-oxo-5,6,7,8-tetrahydro-naphthalen-2-yl)-urea, N-cyclopropylmethyl-5-[3-(5,8-difluoro-2-methyl-quinolin-4-yl)-ureido]-2-methoxy-benzamide, 1-(3-chloro-4-methoxy-phenyl)-3-(5,8-difluoro-2-methyl-quinolin-4-yl)-urea, or a pharmaceutically acceptable salt thereof.

12. A compound according to claim 1, having the formula:

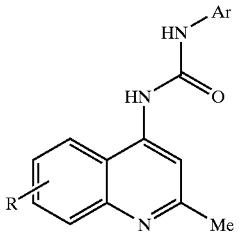

wherein:

| R | Ar |
|---|---|
| H | 3-Br, 4-SMeC$_6$H$_3$ |
| 6,8-diF | 4-MeS, 3-COMe—C$_6$H$_3$ |
| 8-F | 4-MeO, 3-CNC$_6$H$_3$ |
| 5,8-diF | 4-MeO, 3-COMeC$_6$H$_3$ |
| 5,8-diF | 4-Cl, 3-COMeC$_6$H$_3$ |

-continued

| R | Ar |
|---|---|
| 8-F | 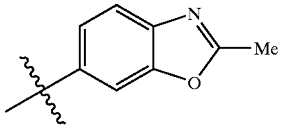 |
| 6,8-diF | 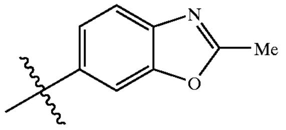 |
| 8-F | 4-MeO, 3-COPrC$_6$H$_3$ |
| 6,8-diF | 3-Cl, 4-OEtC$_6$H$_3$ |
| 6,8-diF | 3-MeO, 4-MeC$_6$H$_3$ |
| 5,8-diF | 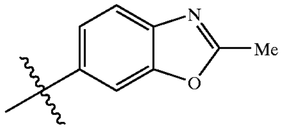 |
| 5,6-diF | 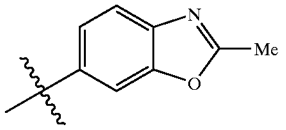 |
| 5,7-diF | 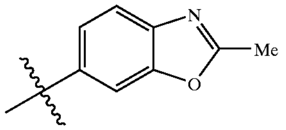 |
| 6-Cl | 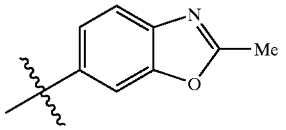 |
| 7,8-diF | 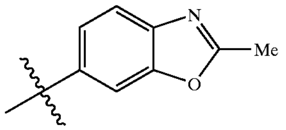 |
| 5,8-diF | 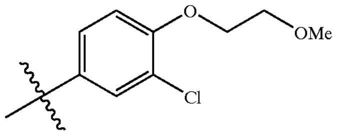 |
| 5,8-diF | 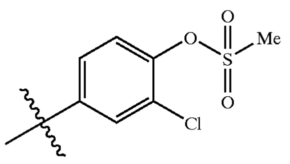 |

or a pharmaceutically acceptable salt thereof.

13. A compound according to claim 1, having the formula:
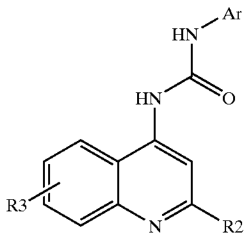
wherein:
| $R^2$ | $R^3$ | Ar |
|---|---|---|
| Me | 8-Et | $4\text{-}NMe_2C_6H_4$ |
| Me | 8-F | 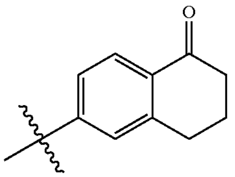 |
| Me | 8-F | 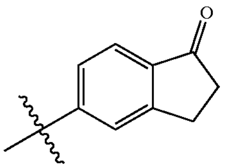 |
| Me | 8-F | $4\text{-}CO_2Et—C_6H_4$ |
| Me | 8-F | 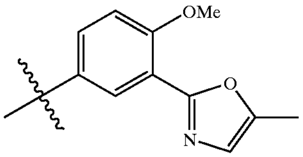 |
| F | H | 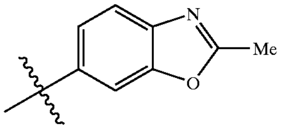 |
| F | H | $4\text{-}NMe_2C_6H_4$ |
| SMe | H | 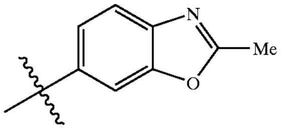 |
| Cl | 8-F | 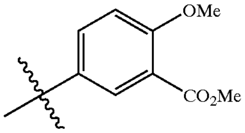 |
| Cl | 8-F | $4\text{-}NMe_2C_6H_4$ |
-continued
| $R^2$ | $R^3$ | Ar |
|---|---|---|
| Cl | 8-F | 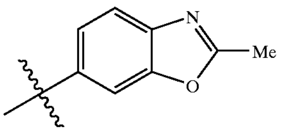 |
| OMe | 8-F | 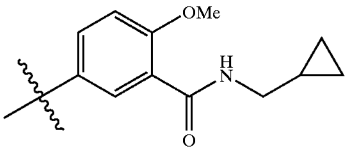 |
| OMe | 8-F | 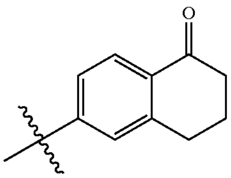 |
| OMe | 8-F | 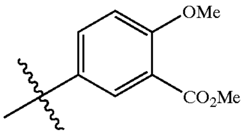 |
| OMe | 8-F | $4\text{-}NMe_2C_6H_4$ |
| OMe | H | 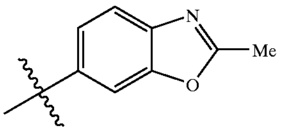 |
| Me | 8-F | 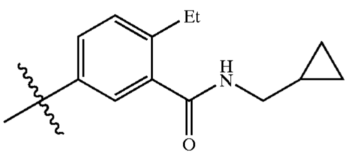 |
| Me | 8-F | 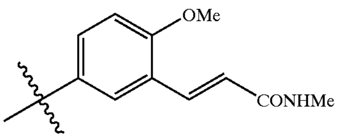 |
| OMe | H | 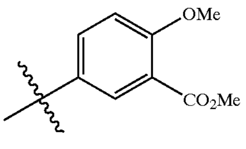 |
or a pharmaceutically acceptable salt thereof.

14. A compound according to claim 1, having the formula:

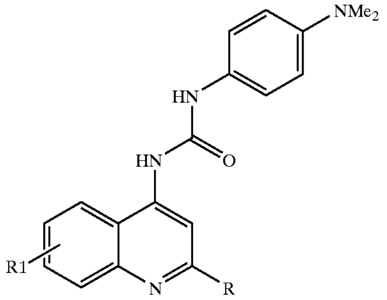

wherein:

| R | $R^1$ |
|---|---|
| Me | 5,8-diF |
| Me | 7,8-diF |
| Me | 6-Me |
| Me | 6,7-diF |
| Me | 8-Me |
| Me | 8-Cl |
| Me | 8-Cl-7-Me |
| Me | 6-F |
| Me | 8-CH—$CH_2$ |
| Me | 5,6-diF |
| Me | 8-Br |

or a pharmaceutically acceptable salt thereof.

15. A compound according to claim 1, having the formula:

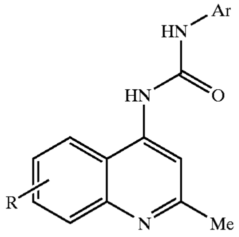

wherein:

| R | Ar |
|---|---|
| 8-F | 3-MeO, 5-$CO_2MeC_6H_3$ |
| 6,8-diF | 4-MeO, 3-$MeOCH_2C_6H_3$ |
| H | 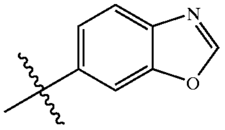 |
| 6,8-diF | 4-MeO, 3-$MeC_6H_3$ |
| 6,8-diF | 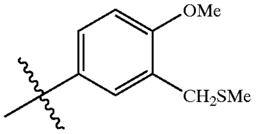 |

or a pharmaceutically acceptable salt thereof.

16. A compound according to claim 1, having the formula:

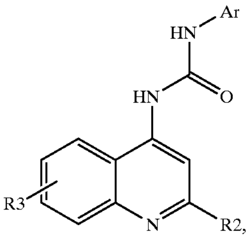

wherein

| R2 | R3 | Ar |
|---|---|---|
| OMe | 8-F | 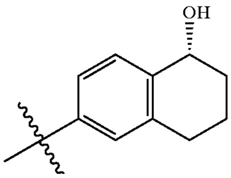 |
| Me | 8-F | 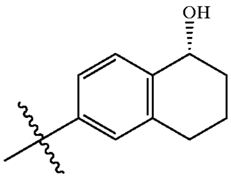 |
| Me | 8-F | 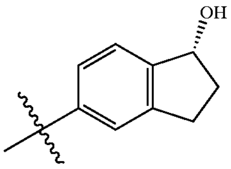 |
| Me | 8-F | 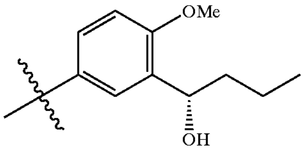 |
| Me | 5,8-diF | 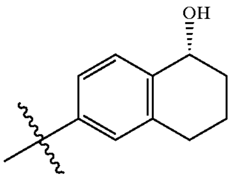 |
| Me | 8-F | 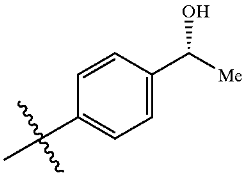 |

or a pharmaceutically acceptable salt thereof.

17. A compound according to claim 1, having the formula:
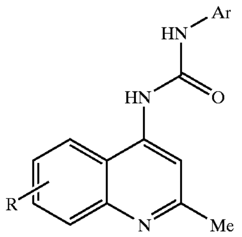
wherein:
| R | Ar |
|---|---|
| 6,8-diF | 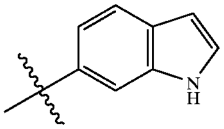 |
| 8-F | 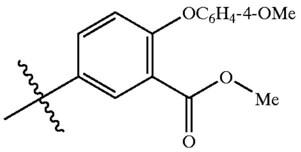 |
| 8-F | 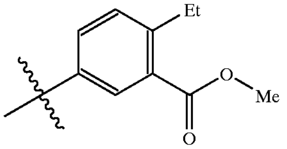 |
| 6,8-diF | 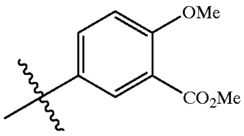 |
| 8-F | 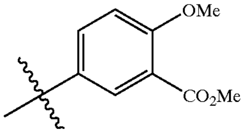 |
| 8-F | 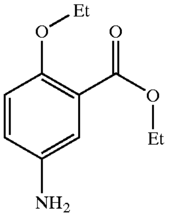 |
| 6,8-diF | 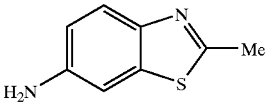 |
-continued
| R | Ar |
|---|---|
| 8-F | 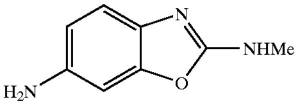 |
| 5,8-diF | 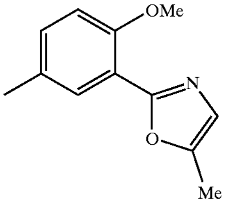 |
or a pharmaceutically acceptable salt thereof.
18. A compound according to claim 1, having the formula:
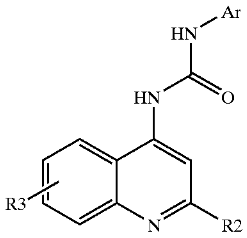
wherein:
| R2 | R3 | Ar |
|---|---|---|
| Cl | 8-F | 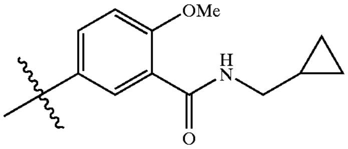 |
| Me | 8-F | 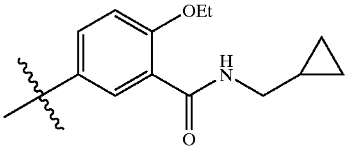 |
| Me | 6,8-diF | 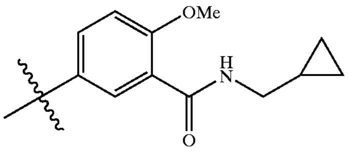 |
| OMe | H | 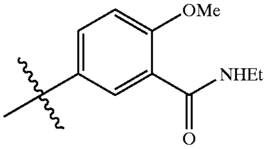 |
or a pharmaceutically acceptable salt thereof.

19. The method according to claims 10, wherein said disease or disorder is selected from obesity, obesity associated with Type II diabetes, and a sleep disorder.

20. The method according to claim 10, wherein said disease or disorder is insomnia.

* * * * *